(12) United States Patent
Myrick

(10) Patent No.: US 8,184,371 B2
(45) Date of Patent: May 22, 2012

(54) THIN FILM INTERFERENCE FILTER AND BOOTSTRAP METHOD FOR INTERFERENCE FILTER THIN FILM DEPOSITION PROCESS CONTROL

(75) Inventor: Michael L. Myrick, Irmo, SC (US)

(73) Assignee: Halliburton Energy Services, Inc., Houston, TX (US)

(*) Notice: Subject to any disclaimer, the term of this patent is extended or adjusted under 35 U.S.C. 154(b) by 28 days.

(21) Appl. No.: 12/819,560

(22) Filed: Jun. 21, 2010

(65) Prior Publication Data
US 2010/0305741 A1 Dec. 2, 2010

Related U.S. Application Data

(62) Division of application No. 11/684,779, filed on Mar. 12, 2007, now abandoned.

(60) Provisional application No. 60/609,406, filed on Sep. 13, 2004.

(51) Int. Cl.
*G02B 1/10* (2006.01)

(52) U.S. Cl. ............ 359/586; 359/584; 359/589

(58) Field of Classification Search ........... 359/586, 359/584, 589; 204/192.13
See application file for complete search history.

(56) References Cited

U.S. PATENT DOCUMENTS

| | | |
|---|---|---|
| 3,717,078 A | 2/1973 | Ogura |
| 3,761,724 A | 9/1973 | Dennis |
| 4,499,378 A | 2/1985 | Miyatake et al. |
| 4,595,832 A | 6/1986 | LaDelfe et al. |
| 4,607,914 A | 8/1986 | Fienup |
| 4,687,337 A | 8/1987 | Stewart et al. |
| 4,704,536 A | 11/1987 | Sugiyama et al. |
| 4,891,574 A | 1/1990 | Nagaya et al. |
| 4,981,332 A | 1/1991 | Smith |
| 5,071,526 A | 12/1991 | Pletcher et al. |
| 5,090,807 A | 2/1992 | Tai |
| 5,137,364 A | 8/1992 | McCarthy |
| 5,223,715 A | 6/1993 | Taylor |
| 5,259,381 A | 11/1993 | Cheung et al. |
| 5,406,082 A | 4/1995 | Pearson et al. |
| 5,504,332 A | 4/1996 | Richmond et al. |
| 5,622,868 A | 4/1997 | Clarke et al. |
| 5,641,962 A | 6/1997 | Perry et al. |

(Continued)

FOREIGN PATENT DOCUMENTS

EP 1969326 A1 9/2008

(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

(Continued)

*Primary Examiner* — Joshua L Pritchett
(74) *Attorney, Agent, or Firm* — Haynes and Boone, LLP

(57) ABSTRACT

A thin film interference filter system includes a plurality of stacked films having a determined reflectance; a modeled monitor curve; and a topmost layer configured to exhibit a wavelength corresponding to one of the determined reflectance or the modeled monitor curve. The topmost layer is placed on the plurality of stacked films and can be a low-index film such as silica or a high index film such as niobia.

27 Claims, 9 Drawing Sheets

U.S. PATENT DOCUMENTS

| | | |
|---|---|---|
| 5,734,098 A | 3/1998 | Kraus et al. |
| 5,737,076 A | 4/1998 | Glaus et al. |
| 5,760,399 A | 6/1998 | Trygstad |
| 5,781,289 A | 7/1998 | Sabsabi et al. |
| 5,831,742 A | 11/1998 | Watson et al. |
| 5,905,571 A | 5/1999 | Butler et al. |
| 5,939,717 A | 8/1999 | Mullins |
| 5,941,821 A | 8/1999 | Chou |
| 5,945,676 A | 8/1999 | Khalil et al. |
| 5,946,088 A | 8/1999 | Aldridge |
| 5,946,089 A | 8/1999 | Duer |
| 5,991,048 A | 11/1999 | Karlson et al. |
| 6,006,585 A | 12/1999 | Forster |
| 6,040,914 A | 3/2000 | Bortz et al. |
| 6,124,937 A | 9/2000 | Mittenzwey et al. |
| 6,137,108 A | 10/2000 | DeThomas et al. |
| 6,176,323 B1 | 1/2001 | Weirich et al. |
| 6,198,531 B1 | 3/2001 | Myrick et al. |
| 6,304,854 B1 | 10/2001 | Harris |
| 6,317,648 B1 | 11/2001 | Sleep et al. |
| 6,347,131 B1 | 2/2002 | Gusterson |
| 6,350,389 B1 | 2/2002 | Fujishima et al. |
| 6,420,708 B2 | 7/2002 | Wilks, Jr. et al. |
| 6,430,513 B1 | 8/2002 | Wang et al. |
| 6,437,326 B1 | 8/2002 | Yamate et al. |
| 6,469,785 B1 | 10/2002 | Duveneck et al. |
| 6,476,384 B1 | 11/2002 | Mullins et al. |
| 6,490,035 B1 | 12/2002 | Folestad et al. |
| 6,517,230 B1 | 2/2003 | Afnan et al. |
| 6,522,945 B2 | 2/2003 | Sleep et al. |
| 6,529,276 B1 | 3/2003 | Myrick |
| 6,600,560 B2 | 7/2003 | Mikkelsen et al. |
| 6,630,663 B2 | 10/2003 | Murphy et al. |
| 6,667,802 B2 | 12/2003 | Faus et al. |
| 6,690,464 B1 | 2/2004 | Lewis et al. |
| 6,697,195 B2 | 2/2004 | Weber et al. |
| 6,707,043 B2 | 3/2004 | Coates et al. |
| 6,711,503 B2 | 3/2004 | Haaland |
| 6,737,654 B2 | 5/2004 | Ducourant |
| 6,741,335 B2 | 5/2004 | Kinrot et al. |
| 6,748,334 B1 | 6/2004 | Perez et al. |
| 6,765,212 B2 | 7/2004 | Goetz et al. |
| 6,771,369 B2 | 8/2004 | Rzasa et al. |
| 6,776,517 B2 | 8/2004 | Afnan et al. |
| 6,798,518 B2 | 9/2004 | Difoggio et al. |
| 6,853,447 B2 | 2/2005 | Goetz |
| 6,870,629 B1 | 3/2005 | Vogel et al. |
| 6,952,267 B2 | 10/2005 | Rarac |
| 6,980,285 B1 | 12/2005 | Hansen |
| 6,982,431 B2 | 1/2006 | Modlin et al. |
| 6,995,840 B2 | 2/2006 | Hagler |
| 7,006,214 B2 | 2/2006 | Rzasa et al. |
| 7,123,844 B2 | 10/2006 | Myrick |
| 7,138,156 B1 | 11/2006 | Myrick et al. |
| 7,145,145 B2 | 12/2006 | Benson |
| 7,173,239 B2 | 2/2007 | DiFoggio |
| 7,245,374 B2 | 7/2007 | Hendriks |
| 7,271,883 B2 | 9/2007 | Newell et al. |
| 7,399,968 B2 | 7/2008 | Lewis et al. |
| 7,405,825 B2 | 7/2008 | Schuurmans et al. |
| 7,411,729 B2 | 8/2008 | Lyama et al. |
| 7,569,354 B2 | 8/2009 | Okano et al. |
| 7,623,233 B2 | 11/2009 | Freese et al. |
| 7,652,767 B2 | 1/2010 | Harsh et al. |
| 7,671,973 B2 | 3/2010 | Van Beek et al. |
| 7,697,141 B2 | 4/2010 | Jones et al. |
| 7,853,104 B2 | 12/2010 | Oota et al. |
| 7,889,346 B2 | 2/2011 | Myrick et al. |
| 7,911,605 B2 | 3/2011 | Myrick et al. |
| 7,920,258 B2 | 4/2011 | Myrick et al. |
| 2001/0034064 A1 | 10/2001 | Turner et al. |
| 2002/0008215 A1 | 1/2002 | Evans |
| 2002/0050567 A1 | 5/2002 | Boudet et al. |
| 2002/0071118 A1 | 6/2002 | Shinbori et al. |
| 2002/0108892 A1 | 8/2002 | Goetz et al. |
| 2002/0109094 A1 | 8/2002 | Goetz et al. |
| 2002/0154315 A1 | 10/2002 | Myrick |
| 2003/0056581 A1 | 3/2003 | Turner et al. |
| 2003/0059820 A1 | 3/2003 | Vo-Dinh |
| 2003/0071988 A1 | 4/2003 | Smith et al. |
| 2003/0094495 A1 | 5/2003 | Knowles et al. |
| 2003/0111606 A1 | 6/2003 | Berghmans et al. |
| 2003/0117628 A1 | 6/2003 | Harju et al. |
| 2003/0202179 A1 | 10/2003 | Larsen et al. |
| 2003/0207023 A1 | 11/2003 | Soni et al. |
| 2004/0012782 A1 | 1/2004 | Mason et al. |
| 2004/0106098 A1 | 6/2004 | Chen et al. |
| 2004/0160601 A1 | 8/2004 | Womble et al. |
| 2004/0197850 A1 | 10/2004 | Baer et al. |
| 2004/0227086 A1 | 11/2004 | Haug et al. |
| 2005/0032235 A1 | 2/2005 | Tummala et al. |
| 2005/0077476 A1 | 4/2005 | Poteet et al. |
| 2005/0087132 A1* | 4/2005 | Dickey et al. .................. 118/715 |
| 2005/0167264 A1* | 8/2005 | Sternbergh et al. ...... 204/192.13 |
| 2005/0251289 A1 | 11/2005 | Bonney et al. |
| 2005/0264815 A1 | 12/2005 | Wechsler et al. |
| 2005/0288906 A1 | 12/2005 | Drennen, III et al. |
| 2006/0035018 A1 | 2/2006 | Sakurai et al. |
| 2006/0051036 A1 | 3/2006 | Treado et al. |
| 2006/0084879 A1 | 4/2006 | Nazarian et al. |
| 2006/0093523 A1 | 5/2006 | Norman |
| 2006/0142955 A1 | 6/2006 | Jones et al. |
| 2006/0153492 A1 | 7/2006 | Treves et al. |
| 2006/0158734 A1 | 7/2006 | Schuurmans et al. |
| 2006/0169902 A1 | 8/2006 | Watanabe |
| 2006/0197015 A1 | 9/2006 | Sterling et al. |
| 2006/0276697 A1 | 12/2006 | Demuth et al. |
| 2007/0035737 A1 | 2/2007 | Andrews et al. |
| 2007/0137292 A1 | 6/2007 | Xian et al. |
| 2007/0201136 A1 | 8/2007 | Myrick |
| 2007/0282647 A1 | 12/2007 | Freese et al. |
| 2007/0294094 A1 | 12/2007 | Alessandrini et al. |
| 2008/0111064 A1 | 5/2008 | Andrews et al. |
| 2008/0231849 A1 | 9/2008 | Myrick |
| 2008/0276687 A1 | 11/2008 | Myrick et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick |
| 2009/0073433 A1 | 3/2009 | Myrick et al. |
| 2009/0097024 A1 | 4/2009 | Blackburn et al. |
| 2009/0140144 A1 | 6/2009 | Myrick et al. |
| 2009/0216504 A1 | 8/2009 | Priore et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0042348 A1 | 2/2010 | Bakker |
| 2010/0073666 A1 | 3/2010 | Perkins et al. |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0211329 A1 | 8/2010 | Farquharson et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0328669 A1 | 12/2010 | Myrick et al. |

FOREIGN PATENT DOCUMENTS

| | | |
|---|---|---|
| EP | 1974201 A1 | 10/2008 |
| EP | 2087328 A2 | 8/2009 |
| EP | 2140238 A1 | 1/2010 |
| JP | 57142546 A | 9/1982 |
| WO | 2004/057284 A1 | 7/2004 |
| WO | 2005/062006 A1 | 7/2005 |
| WO | 2005/062986 A2 | 7/2005 |
| WO | 2006/031733 A2 | 3/2006 |
| WO | 2006/064446 A1 | 6/2006 |
| WO | 2006/137902 A2 | 12/2006 |
| WO | 2007/061435 A1 | 5/2007 |
| WO | 2007/061436 A1 | 5/2007 |
| WO | 2007/061437 A1 | 5/2007 |
| WO | 2007/062202 A1 | 5/2007 |
| WO | 2007/062224 A1 | 5/2007 |

| WO | 2007/064578 A2 | 6/2007 |
| WO | 2008/002903 A2 | 1/2008 |
| WO | 2008/057912 A2 | 5/2008 |
| WO | 2008/057913 A2 | 5/2008 |
| WO | 2008/121684 A1 | 10/2008 |

OTHER PUBLICATIONS

E.B. Martin at al., Process Performance Monitoring Using Multivariate Statistical Process Control', IEE Proc.—Control Theory Appl., vol. 143, No. 2, pp. 132-144, Mar. 1996.

Mandelis et al., "Theory of Photopyroelectric Spectroscopy of Solids", Journal of Applied Physics, vol. 57, No. 9, pp. 4421-4430, 1985.

Zagonel et al., "Multivariate Monitoring of Soybean Oil Ethanolysts by FTIR", Talanta, vol. 63, No. 4, pp. 1021-1025, 2004.

Inon et al., "Combination of Mid- and Near-Infrared Spectroscopy for the Determination of the Quality Properties of Beers", Analytica Chimica Acta, vol. 571, No. 2, pp. 167-174, 2006.

Czarnik-Matusewicz et al., "Temperature-Dependent Water Structural Transitions Examined by Near-IR and Mid-IR Spectra Analyzed by Multivariate Curve Resolution and Two-Dimensional Correlation Spectroscopy", Analytica Chimica Acta, vol. 544, No. 1-2. pp. 15-25, 2005.

Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.

Ghesti et al., "Application of Raman Spectroscopy to Monitor and Quantify Ethyl Esters in Soybean Oil Transesterification", Journal of the American Oil Chemists' Society, vol. 83, pp. 597-601, 2006.

Dereniak et al., *Infrared Detectors and Systems*, John Wiley & Sons: New York, Chapter 9, pp. 395-438, 1996.

Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.

Simcock et al, "Tuning D* with Modified Thermal Detectors", Applied Spectroscopy, vol. 60, No. 12, pp. 1469-1476, 2006.

Lang, "Ferroelectric Polymers and Ceramic-Polymer Composites", Key Engineering Materials, vol. 92-93, pp. 83-142, 1994.

Profeta et al., "Spectral Resolution in Multivariate Optical Computing", Spectrochimica Acta Part A: Molecular and Biomolecular Spectroscopy, vol. 67, pp. 483-502, 2007.

Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.

Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.

Knothe, "Analyzing Biodiesel: Standards and Other Methods", Journal of the American Oil Chemists Society, vol. 83, No. 10, pp. 823-833, 2006.

E.D. Palik, *Handbook of Optical Constants of Solids I*, Academic Press, San Diego, pp. 350-357, 1998.

M.L. Myrick, "Multivariate optical elements simplify spectroscopy", Laser Focus World 38, 91-94, 2002.

O. Soyemi et al., "Design and testing of a multivariate optical element: The first demonstration of muitivariate optical computing for predictive spectroscopy", Anal. Chem. 73, No. 6, pp. 1069-1079, (2001).

M.L. Myrick et al., "A single-element all-optical approach to chemometric prediction", Vib. Spectrosc. 28, 73-81, 2002.

A.M.C. Prakash et al., "Optical regression: a method for improving quantitative precision of multivariate prediction with single channel spectrometers", Chemom. Intell. Lab. Syst. 46, 265-274, 1999.

R.A. Deverse et al., "Realization of the Hadamard multiplex advantage using a programmable optical mask in a dispersive flat-field near-infrared spectrometer", Appl. Spectrosc. 54, 1751-1758, 2000.

F.G. Haibach et al., "Precision in multivariate optical computing", Appl. Optics 43, 2130-2140, 2004.

M.L. Myrick et al., "Application of multivariate optical computing to simple near-Infrared point measurements", Proceedings of the SPIE, Bellingham, VA, US, vol. 4574, pp. 208-215, 2002.

O.S. Heavens, *Optical Properties of Thin Solid Films*, Dover Publications, Inc., Mineola, USA, pp. 62-81, 242-249, 1991.

S. Betancourt et al., "Analyzing Hydrocarbons in the Borehole", Oilfield Review, pp. 54-61, Autumn 2003.

D. Eastwood et al, "Field applications of stand-off sensing using visible/NIR multivariate optical computing", Ground and Air Pollution Monitoring and Remediation, SPIE vol. 4199, pp. 105-114, 2001.

Haibach et al., "On-line Reoptimization of Filter Designs for Multivariate Optical Elements", Applied Optics, vol. 42, No. 10, pp. 1833-1838, Apr. 1, 2003.

Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.

M.P. Nelson et al., "Multivariate optical computation for predictive spectroscopy", SPIE Vo. 3261, pp. 232-243, 1998.

O. Soyemi et al., "A Simple Optical Computing Device for Chemical Analysis", Proceedings of SPIE Vo. 4284, pp. 17-28, 2001.

O. Soyemi et al., "Design of angle tolerant multivariate optical elements for chemical imaging", Applied Optics, vol. 41, No. 10, pp. 1936-1941, Apr. 1, 2002.

O. Soyemi et al., "Nonlinear Optimization Algorithm for Multivariate Optical Element Design", Applied Spectroscopy, vol. 56, No. 4, pp. 477-487, 2002.

O. Soyemi et al., "Novel Filter Design Algorithm for Multivariate Optical Computing", Advanced Environmental and Chemical Sensing Technology, Proceedings of SPIE Vo. 4205, pp. 288-299, 2001.

Strausz et al., "About the Colloidal Nature of Asphaltenes and the MW of Covalent Monomeric Units", American Chemical Society, Energy and Fuels 16, No. 4, pp. 809-822, 2002 (abstract).

N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.

N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.

Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.

Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.

M.P. Nelson et al., "Multivariate optical computation for predictive spectroscopy", Analytical Chemistry, vol. 70, No. 1, pp. 73-82. Jan. 1, 1998.

M.P. Nelson et al., "Fabrication and evaluation of a dimension-reduction fiberoptic system for chemical imaging applications", Review of Scientific Instruments, vol. 70, No. 6, pp. 2836-2843, Jun. 1999.

M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.

M. Groner et al., "Identification of Major Water-Soluble Fluorescent Components of Some Petrochemicals", Marine Pollution Bulletin, vol. 42, No. 10, pp. 935-941, 2001.

M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.

M.L. Myrick et al., "Spectral tolerance determination for multivariate optical element design", Fresenius J Anal Chem, 369:351-355, 2001.

R.J. Priore et al., "Miniature Stereo Spectral Imaging System for Multivariate Optical Computing", Applied Spectroscopy, vol. 58, No. 7, pp. 870-873, 2004.

M.L. Myrick et al., "Use of Molecular Symmetry to Describe Pauli Principle Effects on the Vibration-Rotation Spectroscopy of $CO_2(g)$", Journal of Chemical Education, vol. 81, No. 3, pp. 379-382, Mar. 2004.

M.N. Simcock at al., "Precision in imaging multivariate optical computing", Applied Optics, vol. 46., No. 7, pp. 1066-1080, Mar. 1, 2007.

Ozturk et al., "Filtering Characteristics of Hybrid integrated Polymer and Compound Semiconductor Waveguides", In: Journal of Lightwave Technology, vol. 20, No. 8, pp. 1530-1536, Aug. 2002.

P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.

Mullins et al., "Gas-Oil Ratio of Live Crude Oils Determined by Near-Infrared Spectroscopy", Applied Spectroscopy, vol. 55, No. 2, pp. 197-201, 2001.

\* cited by examiner

THIN FILM INTERFERENCE FILTER AND BOOTSTRAP METHOD FOR INTERFERENCE FILTER THIN FILM DEPOSITION PROCESS CONTROL

CROSS-REFERENCE TO RELATED APPLICATIONS

This application is a divisional application of U.S. application having Ser. No. 11/684,779, which is the U.S. Nationalization of International Application No. PCT/US2005/032420 having an international filing date of Sep. 13, 2005, which claims benefit of U.S. Provisional Patent Application, Ser. No. 60/609,406, entitled "Bootstrap Method for Interference Filter Thin Film Deposition Process Control," filed Sep. 13, 2004.

STATEMENT OF FEDERALLY SPONSORED RESEARCH OR DEVELOPMENT

This invention was made with Government support under grant number F33615-00-2-6059 awarded by the United States Air Force Research Laboratory. The Government has certain rights in this invention.

FIELD OF THE INVENTION

The present invention relates to thin film optical devices. More particularly, the invention relates to complex interference filters.

BACKGROUND OF THE INVENTION

Highly accurate optical interference filters can be manufactured using thin film deposition processes. These optical interference filters are used for multivariate optical computing, multiple-band-pass, and the like and can exhibit complex optical spectra defined over a range of wavelengths. These filters are typically constructed by depositing alternating layers of transparent materials where one layer possesses a much larger refractive index relative to the other layer. Theoretically, the proper choice of composition, thickness and quantity of layers could result in a device with any desired transmission spectrum.

Among the simplest devices is the single cavity bandpass filter; i.e., the thin-film form of an etalon. This device consists of three sets of layers. The first stack is a dielectric mirror, a next thicker layer forms a spacer, and a second stack forms another dielectric mirror. The mirror stacks are typically fabricated by depositing alternating transparent materials that have an optical thickness that is one quarter of the optical wavelength of light.

To achieve theoretical optical performance, each layer must possess a precise and specific physical thickness and refractive index. Any nonuniformity in the deposition of the layers can affect the spectral placement and transmission or reflection characteristics of the device. A design that requires very tight manufacturing tolerances over large substrate areas could result in the costly rejection of many devices. Given these manufacturing limits, it would be desirable to analyze the devices after construction and alter the devices that do not meet a predetermined optical transmission or reflection specification by some electrical or mechanical means. For example, if the peak transmission wavelength of a manufactured optical bandpass cavity filter was slightly out of tolerance, it would be desirable to have a mechanism or process for shifting the peak back to the desired spectral location. It is also desirable that the optical filters have precise rejection bands and passbands that are electrically or mechanically selectable.

Mechanical methods of achieving a variable transmission spectrum device are well known. This includes changing a prism or grating angle, or altering the optical spacing between mirrors of an etalon. To overcome the performance, size and cost disadvantages of using mechanical schemes, many have conceived of electrical methods for varying a transmission spectrum. For example, U.S. Pat. No. 5,150,236, issued Sep. 22, 1992 to Patel, discloses a tunable liquid crystal etalon filter. The liquid crystal fills the space between dielectric mirrors. Electrodes on the mirrors are used to apply an electric field, which changes the orientation of the liquid crystal that changes the optical length for tuning. The change in the optical length corresponds to a change in the location of the passband. U.S. Pat. No. 5,103,340, issued Apr. 7, 1992 to Done et al., discloses piezoelectric elements placed outside the optical path that are used to change the spacing between cascaded cavity filters. Furthermore, U.S. Pat. No. 5,799,231, issued Aug. 25, 1998 to Gates et al., discloses a variable index distributed mirror. This is a dielectric mirror with half of the layers having a variable refractive index that is matched to other layers. Changing the applied field increases the index difference that increases the reflectance. The mathematics that describes the transmission characteristics of multilayer films composed of electro-optic and dielectric materials are well known.

Another electrically actuated thin film optical filter uses a series of crossed polarizers and liquid crystalline layers that allow electrical controls to vary the amount of polarization rotation in the liquid by applying an electric field in such a way that some wavelengths are selectively transmitted. However, these electrically actuated thin film optical filters have the characteristic that the light must be polarized and that the frequencies of light not passed are absorbed, not reflected. Another electrically actuated thin film optical device is the tunable liquid crystal etalon optical filter. The tunable liquid crystal etalon optical filter uses a liquid crystal between two dielectric mirrors.

The common cavity filter, such as the etalon optical filter, is an optical filter with one or more spacer layers that are deposited in the stack and define the wavelength of the rejection and pass bands. The optical thickness of the film defines the placement of the passband. U.S. Pat. No. 5,710,655, issued Jan. 20, 1998 to Rumbaugh et al., discloses a cavity thickness compensated etalon filter.

In the tunable liquid crystal etalon optical filter, an electric field is applied to the liquid crystal that changes the optical length between the two mirrors so as to change the passband of the etalon. Still another tunable optical filter device tunes the passband by using piezoelectric elements to mechanically change the physical spacing between minors of an etalon filter.

Bulk dielectrics are made by subtractive methods like polishing from a larger piece; whereas thin film layer are made by additive methods like vapor or liquid phase deposition. A bulk optical dielectric, e.g., greater than ten microns, disposed between metal or dielectric mirrors suffers from excessive manufacturing tolerances and costs. Moreover, the bulk material provides unpredictable, imprecise, irregular, or otherwise undesirable passbands. These electrical and mechanical optical filters disadvantageously do not provide precise rejection bands and passbands that are repeatably manufactured.

In an attempt to avoid some of the foregoing problems, modeling of interference filters can be conducted during on-line fabrication with in-situ optical spectroscopy of the filter during deposition. The current state of the art for on-line correction of the deposition involves fitting the observed spectra to a multilayer model composed of "ideal" films based on a model for each film. The resulting model spectra are approximations of the actual spectra. To use reflectance as an example: the measured reflectance of a stack of films can be approximately matched to a theoretical reflectance spectrum by modeling. Layers remaining to be deposited can then be adjusted to compensate for errors in the film stack already deposited, provided the film stack has been accurately modeled. However, films vary in ways that cannot be readily modelled using any fixed or simple physical model. Heterogeneities in the films that cannot be predicted or compensated by this method cause the observed spectra to deviate more and more from the model. This makes continued automatic deposition very difficult; complex film stacks are therefore very operator-intensive and have a high failure rate. To improve efficiency in fabrication, laboratories that fabricate these stacks strive to make their films as perfectly as possible so the models are as accurate as possible.

As outlined above, many thin films are usually designed in a stack to produce complex spectra and small variations in deposition conditions make it difficult to accurately model in situ film spectra for feedback control of a continuous deposition process because it is practically impossible to obtain full knowledge of the detailed structure of the stack from reflectance, transmittance, ellipsometry, mass balance or other methods. Thus, a thin film interference filter is needed that is less difficult to manufacture, which will address varying refractive indices of thin films and varying absorptions with deposition parameters.

BRIEF SUMMARY OF INVENTION

In general, the present invention is directed to a layered, thin film interference filter and related bootstrap methods. A bootstrap method according to one aspect of the invention permits a user to focus on a single layer of a film stack as the layer is deposited to obtain an estimate of the properties of the stack. Although the single layer model is a guideline and not a basis for compensating errors, only the most-recently-deposited layer—and not the already-deposited film stack—need be modeled according to an aspect of the present invention. Thus, the user can neglect deviations of the stack from ideality for all other layers. The single-layer model can then be fit exactly to the observed spectra of the film stack at each stage of deposition to allow accurate updating of the remaining film stack for continued deposition.

The present invention works with any type of films, whether absorbing or non-absorbing, and regardless of whether the control of the deposition conditions are state-of-the-art or not. The methods of the invention are relatively straightforward, and a resultant thin film interference filter is economical to produce and use.

According to a particular aspect of the invention, a method using experimental measurements to determine reflectance phase and complex reflectance for arbitrary thin film stacks includes the steps of determining reflectance of a stack of a plurality of films before depositing a topmost layer; considering a modeled monitor curve for a wavelength of a high-index layer; and discarding a plurality of monitor curves without maxima in their reflectance during the topmost layer deposition. In this aspect of the invention, the topmost layer can be a niobia layer.

The exemplary method can also include the steps of determining an anticipated standard deviation in $\phi_k$ for a plurality of monitor wavelengths in the niobia layer and discarding any with $\sigma$ greater than 0.9 degrees. Another step in this aspect is computing expected error in $\delta$ for wavelengths with $\sigma$ less than 0.9 degrees at a target thickness of the niobia layer. When no wavelengths have an error less than 0.9 degrees, a further step according to this method is to proceed with a full model deposition of the niobia layer. When there are no maxima in the reflectance of each of the plurality of monitor curves, another step according to the exemplary method is to use only the modeled monitor curve during the topmost layer deposition.

The method according to this aspect of the invention can also include the step of computing a value of $\delta$ for all wavelengths based on a value calculated for the monitor wavelength.

The method according to this aspect of the invention can farther include the step of computing two possible values of phase angle for each wavelength other than the monitor wavelength.

Additional steps according to the exemplary method include using information extracted from the model for $r_k$ at each wavelength and the computed best value of $\delta$, and computing an estimated standard deviation of phase at all wavelengths except the monitor.

The method may further include the steps of using the computed phase closest to the model phase for $r_k$ at each wavelength, measured $R_f$ and $R_k$ values and the computed best value of $\delta$, and computing the estimated standard deviation of phase at all wavelengths for which the magnitude of $r_k$ was estimated other than the monitor.

Further steps according to the exemplary method include the steps of determining if a phase error estimate is less than about 1.3 degrees and averaging calculated and modeled reflectance and phase values to obtain a new value for use in subsequent modeling at that wavelength.

In yet another aspect according to the exemplary method, the topmost layer can be a silica film. Accordingly, the method can include the step of replacing the magnitude of the amplitude reflectance at each wavelength with $\sqrt{R_k}$ whenever measuring a latest depositing silica film having an intensity reflectance greater than 9%. The method can also include the step of determining if a phase error estimate is less than about 1.3 degrees when the magnitude of the amplitude reflectance at each wavelength has been replaced with $\sqrt{R_k}$ and averaging calculated and modeled reflectance and phase values to obtain a new value for use in subsequent modeling at that wavelength.

In yet another aspect of the invention, a method for correcting thin film stack calculations for accurate deposition of complex optical filters can include the steps of determining phase angle $\phi k$ at a monitor wavelength from $|r_k'|$ and Rk using a first equation expressed as $$\cos(\pm\phi_k) = \frac{|r_k'|^2(1 + R_k|r_2|^2) - |r_2|^2 - R_k}{2|r_2|\sqrt{R_k}\,(1 - |r_k'|^2)};$$

and estimating $r_k'$ using a second equation $$r_k' = \frac{r_k - r_2}{1 - r_2 r_k};$$

and obtaining a value for phase at a monitor wavelength.

Still another aspect of the invention includes a method for automated deposition of complex optical interference filters including the steps of determining from a measurement of intensity reflectance at a topmost interface a phase angle φ at an interface k according to an equation expressed as:

$$\cos(\phi_k) = \left( \frac{A(1+r_2^2)\sin(\delta) \pm B\cos(\delta)}{C} \right)$$

$$A = R_f + r_2^4(R_f - R_k) - R_k + 2r_2^2((1-R_f)(1+R_k)\cos(2\delta) - (1-R_fR_k))$$

$$B = \sqrt{D(1+r_2^{12}) + F(r_2^2 + r_2^{10}) + G(r_2^4 + r_2^8) + Hr_2^6}$$

$$C = \sin(\delta)(4r_2(1-R_f)R_k^{1/2}(2r_2^2\cos(2\delta) - 1 - r_2^4))$$

$$D = -(R_f - R_k)^2$$

$$F = 2\begin{pmatrix} R_k(2+R_k) + R_f^2(1+2R_k) + 2R_f(1-5R_k + R_k^2) - \\ 2(1-R_f)(1-R_k)(R_f+R_k)\cos(2\delta) \end{pmatrix}$$

$$G = -6 - 4R_f - 5R_f^2 - 4R_k + 38R_fR_k - 4R_f^2R_k - 5R_k^2 - 4R_fR_k^2 -$$
$$6R_f^2R_k^2 + 8(1-R_f^2)(1-R_k^2)\cos(2\delta) - 2(1-R_f)^2(1-R_k)^2\cos(4\delta)$$

$$H = 4\begin{pmatrix} 3 + 2R_f^2 - 10R_fR_k + 2R_k^2 + 3R_f^2R_k^2 - \\ 2(1-R_f)(1-R_k)(2+R_f+R_k+2R_fR_k)\cos(2\delta) + \\ (1-R_f)^2(1-R_k)^2\cos(4\delta) \end{pmatrix}$$

According to this exemplary method, a process control for a deposition system is bootstrapped by detaching the deposition system from all but the topmost interface.

The method can further include the step of validating two resultant solutions according to the expression:

$$R_f = \frac{2r_2^2 + R_k(1+r_2^4) + 2r_2Q}{1 + r_2^4 + 2r_2^2R_k + 2r_2Q}$$

$$Q = r_2^2R_k^{1/2}\cos(2\delta + \phi_k) +$$
$$R_k^{1/2}\cos(2\delta - \phi_k) - r_2(1+R_k)\cos(2\delta) - (1+r_2^2)R_k^{1/2}\cos(\phi_k)$$

The method can also include the step of averaging calculated and modeled reflectance and phase values to obtain a new value to be used in all future modeling at a given wavelength.

According to another aspect of the invention, a thin film interference filter system includes a plurality of stacked films having a determined reflectance; a modeled monitor curve; and a topmost layer configured to exhibit a wavelength corresponding to one of the determined reflectance or the modeled monitor curve, the topmost layer being disposed on the plurality of stacked films. The topmost layer according to this aspect can be a low-index film such as silica or a high index film such as niobia.

Other aspects and advantages of the invention will be apparent from the following description and the attached drawings, or can be learned through practice of the invention.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

DETAILED DESCRIPTION OF THE INVENTION

Figure 1:
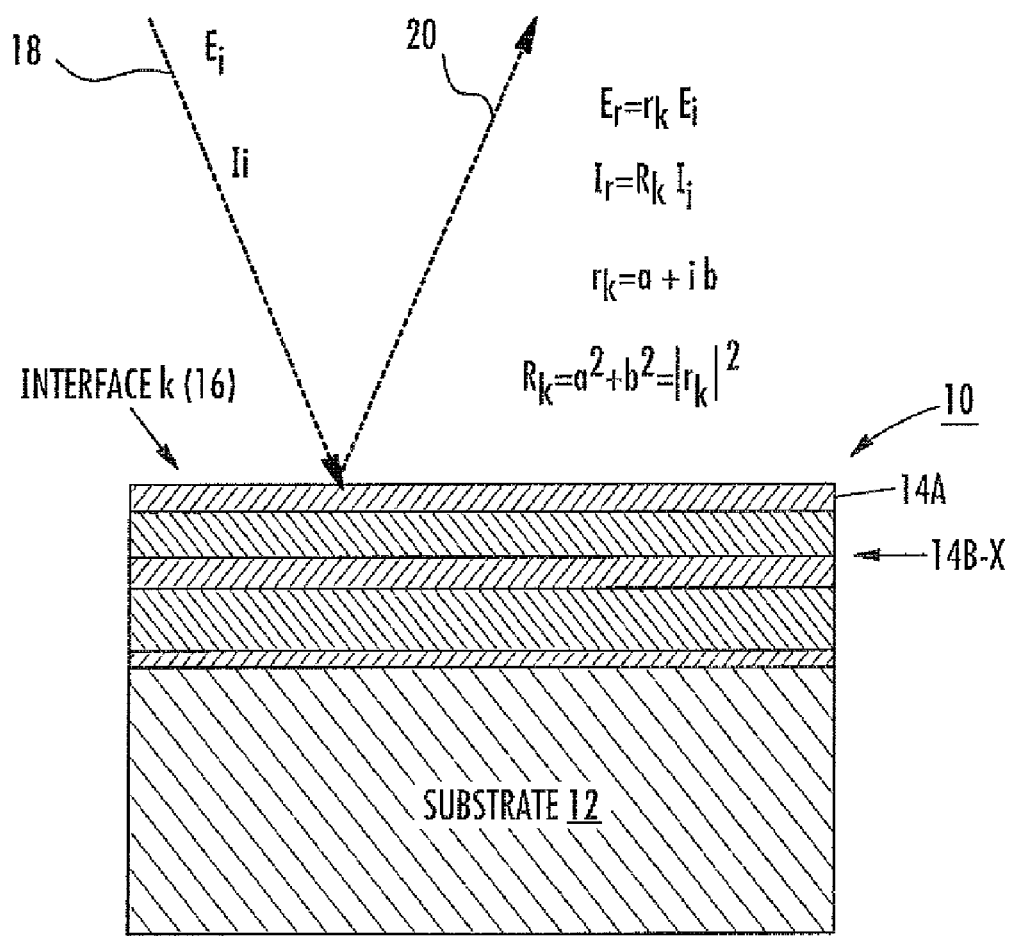
FIG. 1 is a schematic, cross sectional view of a stack of films according to an aspect of the invention.

Detailed reference will now be made to the drawings in which examples embodying the present invention are shown. Repeat use of reference characters in the drawings and detailed description is intended to represent like or analogous features or elements of the present invention.

The drawings and detailed description provide a full and detailed written description of the invention and the manner and process of making and using it, so as to enable one skilled in the pertinent art to make and use it. The drawings and detailed description also provide the best mode of carrying out the invention. However, the examples set forth herein are provided by way of explanation of the invention and are not meant as limitations of the invention. The present invention thus includes modifications and variations of the following examples as come within the scope of the appended claims and their equivalents.

Turning now to the figures, FIG. 1 shows a thin film interference filter 10, which broadly includes a substrate 12 upon which a stack of films 14A-X is deposited (where x represents a theoretically infinite number of film layers). As shown, the last (alternatively, final, top or topmost) deposited film is designated by the alphanumeral 14A while previously deposited or lower level films are designated 14B-X. An incoming ray 18 is shown in FIG. 1 being reflected at an interface 16 (also referred to herein as top or top surface and when mathematically referenced as k). The reflected ray is designated by the number 20. For simplicity, any contribution from multiple incoherent reflections in the substrate 12 is ignored in the following discussion and only reflections with respect to the film stack 14A-X are described.

Typically, reflectance of the top surface 16 is obtained using a matrix calculation that is in turn built from the characteristic matrices of each of the preceding films 14A-X. As shown in FIG. 1, a computed value of an electric field amplitude reflectance $r_k$ is obtained by optimizing the thickness of the topmost film 14A to provide the best fit over the full spectrum consistent with an understanding of the existing film stack 14B-X. The calculated value of $r_k$ can be considered an estimate of the actual value of $r_k$ exhibited by the film stack 14A-X.

Since $r_k$ is a complex value, it cannot be measured directly. Normal Matrix-Type Calculations:

For standard calculations, the complex reflectance of a stack of films is computed using the admittances of the incident medium (often air), and the first interface of the stack.

For s and p polarization, this reflectance is:

$$r_s^{(f_1)} = \frac{-\eta_s^{(inc)} - \eta_s^{(f_1)}}{-\eta_s^{(inc)} + \eta_s^{(f_1)}} \qquad (6)$$

$$r_p^{(f_1)} = \frac{\eta_p^{(inc)} - \eta_p^{(f_1)}}{\eta_p^{(inc)} + \eta_p^{(f_1)}}.$$

where the subscript s or p indicates for s or p-polarized light, η is a complex admittance, the superscript "inc" indicates the incident medium and ($f_1$) indicates the first interface the light strikes when coming from the incident medium.

For s and p polarized light, the admittances of the incident media are written:

$$\eta_s^{(inc)} = \sqrt{\varepsilon_{inc} - \varepsilon_{inc}\sin^2(\theta_{inc})} \qquad (7)$$

$$\eta_p^{(inc)} = \frac{\varepsilon_{inc}}{\sqrt{\varepsilon_{inc} - \varepsilon_{inc}\sin^2(\theta_{inc})}}.$$

where $\in$ indicates a complex dielectric constant, and $\theta_{inc}$ is the angle of incidence in the medium of incidence, The problematic part of the calculation is how to express the admittance of the initial interface. The matrix calculation proceeds by relating the admittance of the initial interface to that of the second interface, the admittance of the second to the third, etcetera, through a series of 2×2 matrices, until the calculation is related to the final interface. At the final interface, the admittance (ratio of magnetic to electric fields) is equal to the admittance of the exit medium, which is simple to compute because there is only a single ray (the transmitted ray), rather than rays propagating in two different directions.

For a single layer stack the admittance of the initial interface is related to the exit medium admittance according to the following equations:

$$\begin{pmatrix} E_x^{(f_1)} \\ H_y^{(f_1)} \end{pmatrix} = \begin{pmatrix} s_{11} & s_{12} \\ s_{21} & s_{22} \end{pmatrix} \begin{pmatrix} E_x^{(f_2)} \\ H_y^{(f_2)} \end{pmatrix} = \begin{pmatrix} s_{11} & s_{12} \\ s_{21} & s_{22} \end{pmatrix} \begin{pmatrix} E_x^{(3)} \\ H_y^{(3)} \end{pmatrix} \qquad (8)$$

$$\therefore \begin{pmatrix} E_x^{(f_1)}/E_x^{(3)} \\ H_y^{(f_1)}/E_x^{(3)} \end{pmatrix} = \begin{pmatrix} s_{11} & s_{12} \\ s_{21} & s_{22} \end{pmatrix} \begin{pmatrix} 1 \\ -\eta_s^{(3)} \end{pmatrix}$$

$$\therefore \eta_s^{(f_1)} = \frac{H_y^{(f_1)}}{E_x^{(f_1)}} = \frac{s_{11} + s_{12}(-\eta_s^{(3)})}{s_{21} + s_{22}(-\eta_s^{(3)})}.$$

In these equations, the superscript (3) indicates the exit medium. The admittance of the exit medium for s-polarized light is given by $\eta_s^{(3)} = \sqrt{\varepsilon_3 - \varepsilon_{inc}\sin^2(\theta_{inc})}$. The negative sign in front of $\eta_s^{(3)}$ in the second line results from defining light as propagating in the negative z direction. For s-polarized light, the magnetic and electric fields are of opposite signs in this case. For p-polarized light, they are of the same sign. The 2×2 matrix for the single film is described below.

For p-polarized light, the admittance of the initial interface is arrived at in the same way:

$$\begin{pmatrix} E_y^{(f_1)} \\ H_x^{(f_1)} \end{pmatrix} = \begin{pmatrix} p_{11} & p_{12} \\ p_{21} & p_{22} \end{pmatrix} \begin{pmatrix} E_y^{(f_2)} \\ H_x^{(f_2)} \end{pmatrix} = \begin{pmatrix} p_{11} & p_{12} \\ p_{21} & p_{22} \end{pmatrix} \begin{pmatrix} E_y^{(3)} \\ H_x^{(3)} \end{pmatrix} \qquad (9)$$

$$\therefore \begin{pmatrix} E_y^{(f_1)}/E_y^{(3)} \\ H_x^{(f_1)}/E_y^{(3)} \end{pmatrix} = \begin{pmatrix} p_{11} & p_{12} \\ p_{21} & p_{22} \end{pmatrix} \begin{pmatrix} 1 \\ \eta_p^{(3)} \end{pmatrix}$$

$$\therefore \eta_p^{(f_1)} = \frac{H_x^{(f_1)}}{E_y^{(f_1)}} = \frac{p_{11} + p_{12}\eta_p^{(3)}}{p_{21} + p_{22}\eta_p^{(3)}}.$$

For p-polarized light, the admittance of the exit medium is written as $\eta_p^{(3)} = \varepsilon_3/\sqrt{\varepsilon_3 - \varepsilon_{inc}\sin^2(\theta_{inc})}$. The 2×2 matrices for s and p polarizations are defined by:

$$s_{12} = s_{22} = p_{11} = p_{22} = \cos(\delta_{film}) \qquad (10)$$

$$s_{12} = \frac{-i}{\eta_s^{(film)}}\sin(\delta_{film})$$

$$s_{21} = -i\eta_s^{(film)}\sin(\delta_{film})$$

$$p_{12} = \frac{i}{\eta_p^{(film)}}\sin(\delta_{film})$$

$$p_{21} = i\eta_p^{(film)}\sin(\delta_{film}).$$

In these equations, the admittances of the film are written in the same form as the admittances of the exit medium given above, but with $\in_{film}$ replacing $\in_3$. The value δfilm is the phase thickness of the film, given by $$\delta_{film} = \frac{2\pi d_{film}\sqrt{\varepsilon_{film} - \varepsilon_{inc}\sin^2(\theta_{inc})}}{\lambda_0}. \qquad (11)$$

where dfilm is the physical thickness of the film and λ0 is the free-space wavelength of the incident light.

If there are multiple films, the matrix for a stack of films is obtained from $$S = \begin{pmatrix} s_{11} & s_{12} \\ s_{21} & s_{22} \end{pmatrix} = \prod_{inc}^{exit} S_{films}. \qquad (12)$$

where the product is over the 2×2 matrices of each individual film from the entrance to the exit. The final product matrix is used as though it described a single equivalent layer.

Notably in the preceding calculation, the matrices describing the film are used as "transfer" matrices. This permits propagation of the calculation of the admittance of the initial interface down through a stack of films. The downward propagation is stopped at the substrate because, once there are no longer rays propagating in both directions, a simple form (the admittance of the exit medium) can be written. Thus, the matrices allow an impossible calculation to be related to a simplified calculation via a 2×2 matrix.

A critical piece of understanding results from the following discussion. Referring to Equation 8 above for s polarization, $-\eta_s^{(3)}$, is the admittance of the final interface (thus the basis for preserving the negative sign). In comparison, p polarization, $\eta_p^{(3)}$, in Equation 6 is the admittance of the final interface. Thus, both the s and p calculation of admittance for the initial interface can be written in a generic form:

$$\eta^{(f_1)} = \frac{H^{(f_1)}}{E^{(f_1)}} = \frac{m_{11} + m_{12}\eta^{(f_\omega)}}{m_{21} + m_{22}\eta^{(f_\omega)}}. \qquad 13$$

where the matrix elements are for either the s or p matrices, and $\eta^{(f_\omega)}$ is the admittance of the final interface. The final interface is always chosen because a simple expression for its admittance can be written in terms of the admittance of the exit medium.

A Bootstrap Method according to an aspect of the invention depends on finding experimental values for the complex reflectance at a given interface in a film stack. Thus, an initial matter of using the amplitude reflectance of a film surface alone to complete the matrix calculation for the films above the film surface in question will be described.

Solving the Top of the Stack

Figure 2:
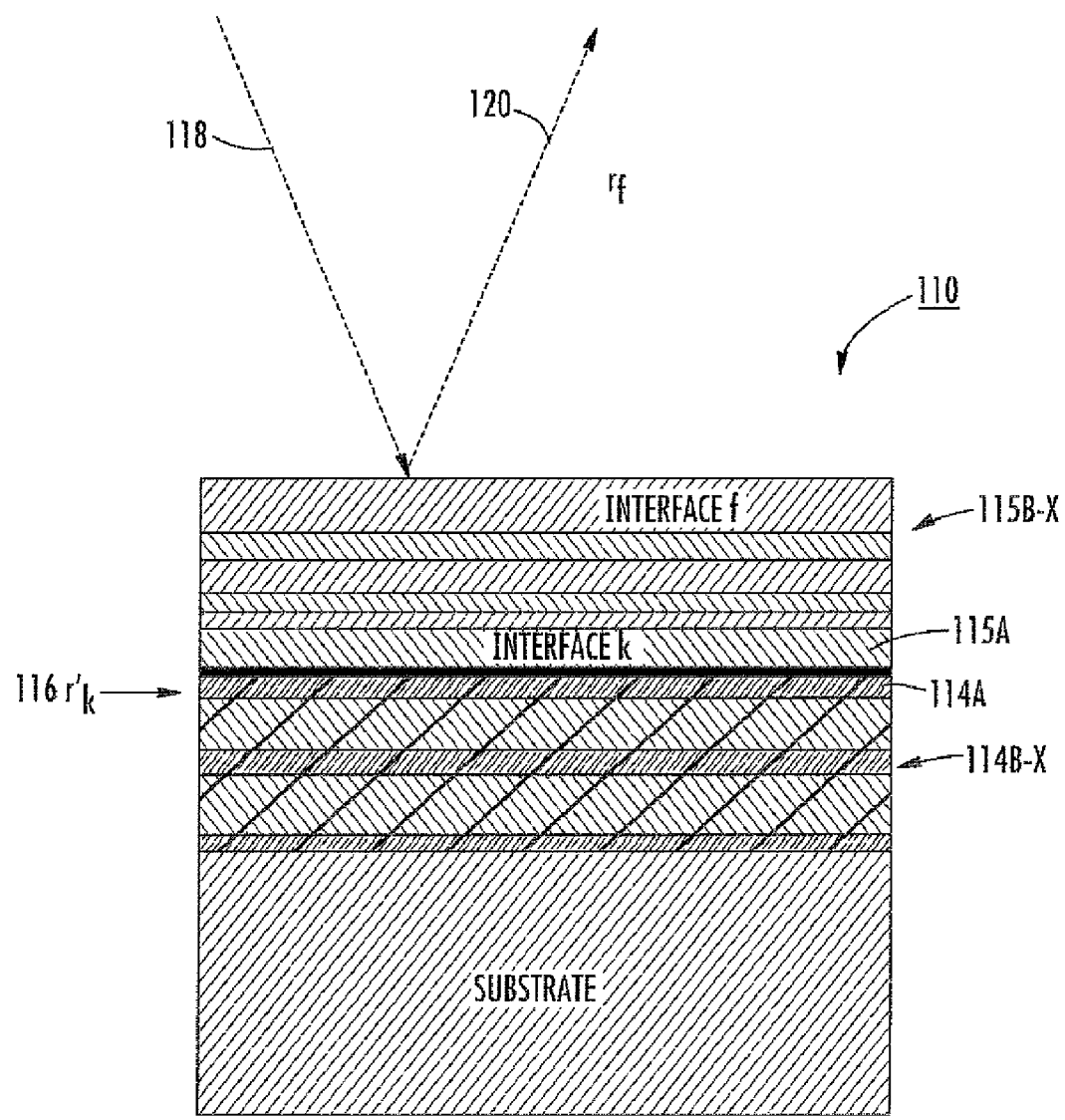
FIG. 2 is a schematic, cross sectional view of a stack of films similar to FIG. 1 showing an internal interface in the stack of films according to another aspect of the invention.

Turning now to a problem illustrated in FIG. 2, reflectance at some interface 160 (mathematically, k') below a film stack 115A-X is assumed. Earlier layers 114A-X are shown "grayed out" and with diagonal lines to indicate a vague idea of what those layers 114A-X are. The reflectance of the "known" layer 114A differs in value from the reflectance described above (thus, a "prime" symbol on k at the interface 116 indicates the different value). However, it is still desirable to be able to compute the reflectance spectrum of the stack of films 115A-X layered on top of the "known" layer 114A.

It is possible to compute the spectrum of a film stack when the amplitude reflectance at one interface at the bottom is known. To appreciate how this calculation is done, it is useful to review the known method for calculating reflectance and understand what the assumptions are.

If the amplitude reflectivity for an interface k (which can be any interface, including the final interface) is known, an equivalent expression to Equation 13 can be obtained in terms of the admittance of that interface in lieu of carrying the calculation all the way down to the substrate. The admittance for the $k^{th}$ interface can be written as follows:

$$\text{for } s: \begin{cases} \begin{pmatrix} E_x^{(f_k)} \\ H_y^{(f_k)} \end{pmatrix} = \begin{pmatrix} (r_k' + 1)E_x^{(i_2)} \\ (r_k' - 1)\eta_s^{(2)}\hat{E}_x^{(i_2)} \end{pmatrix} \\ \eta_s^{(f_k)} = \eta_s^{(2)}\frac{(r_k' - 1)}{(r_k' + 1)} \end{cases} \qquad 14$$

$$\text{for } p: \begin{cases} \begin{pmatrix} E_y^{(f_k)} \\ H_x^{(f_k)} \end{pmatrix} = \begin{pmatrix} (1 + r_k')E_y^{(i_2)} \\ (1 - r_k')\eta_p^{(2)}E_y^{(i_2)} \end{pmatrix} \\ \eta_p^{(f_k)} = \eta_p^{(2)}\frac{(1 - r_k')}{(1 + r_k')} \end{cases}.$$

In this expression for the admittance of the known interface, "2" indicates the admittance of the film deposited directly on the known interface. This can then used as the starting point for computing the reflectance of a stack of films above the known interface. The admittance of the top interface can be written as:

$$\eta_s^{(f_1)} = \frac{H_y^{(f_1)}}{\hat{E}_x^{(f_1)}} = \frac{s_{21}' + s_{22}'\eta_s^{(f_k)}}{s_{11}' + s_{12}'\eta_s^{(f_k)}} = \frac{s_{21}' + s_{22}'\eta_s^{(2)}\left(\frac{r_k'-1}{r_k'+1}\right)}{s_{11}' + s_{12}'\eta_s^{(2)}\left(\frac{r_k'-1}{r_k'+1}\right)} \qquad 15$$

$$\eta_p^{(f_1)} = \frac{H_x^{(f_1)}}{\hat{E}_y^{(f_1)}} = \frac{p_{21}' + p_{22}'\eta_p^{(f_k)}}{p_{11}' + p_{12}'\eta_p^{(f_k)}} = \frac{p_{21}' + p_{22}'\eta_p^{(2)}\left(\frac{1-r_k'}{1+r_k'}\right)}{p_{11}' + p_{12}'\eta_p^{(2)}\left(\frac{1-r_k'}{1+r_k'}\right)}.$$

In addition to the change in definition for the terminal interface of the calculation, another difference is the matrix elements come from a modified 2×2 matrix for the film stack. The modified matrix is computed as:

$$S' = \begin{pmatrix} s_{11}' & s_{12}' \\ s_{21}' & s_{22}' \end{pmatrix} = \prod_{inc}^{k+} S_{films} \qquad 16$$

$$P' = \begin{pmatrix} p_{11}' & p_{12}' \\ p_{21}' & p_{22}' \end{pmatrix} = \prod_{inc}^{k+} P_{films}.$$

where the product is taken in the order of incident light penetrating the stack as before, but the calculation ends with the film deposited directly onto the known interface. The symbol k+ in Equation 16 is used to indicate that the product terminates with a layer 115A directly above the known interface 114A. The change is a significant one, in that the 2×2 matrices for any of the films below the known interface 114A no longer have to be computed.

Returning to Equation 6, the following can be expressed:

$$r_s^{(f_1)} = \frac{\eta_s^{(inc)}s_{11}'(1+r_k') - \eta_s^{(inc)}\eta_s^{(2)}s_{12}'(1-r_k') +}{\eta_s^{(inc)}s_{11}'(1+r_k') - \eta_s^{(inc)}\eta_s^{(2)}s_{12}'(1-r_k') -} \qquad 17$$
$$\frac{s_{21}'(1+r_k') - \eta_s^{(2)}s_{22}'(1-r_k')}{s_{21}'(1+r_k') + \eta_s^{(2)}s_{22}'(1-r_k')}$$

$$r_p^{(f_1)} = \frac{\eta_p^{(inc)}p_{11}'(1+r_k') + \eta_p^{(inc)}\eta_p^{(2)}p_{12}'(1-r_k') -}{\eta_p^{(inc)}p_{11}'(1+r_k') + \eta_p^{(inc)}\eta_p^{(2)}p_{12}'(1-r_k') +}$$
$$\frac{p_{21}'(1+r_k') - \eta_p^{(2)}p_{22}'(1-r_k')}{p_{21}'(1+r_k') + \eta_p^{(2)}p_{22}'(1-r_k')}.$$

Note that these equations feature a complex quantity called $r_k'$, which, as mentioned above, is not the same as $r_k$, the amplitude reflectance of the top of the film stack before the topmost layer was added. The two things are related to one another, however, as evident in the following discussion.

Amplitude Reflectance of a Buried Interface

Figure 3:
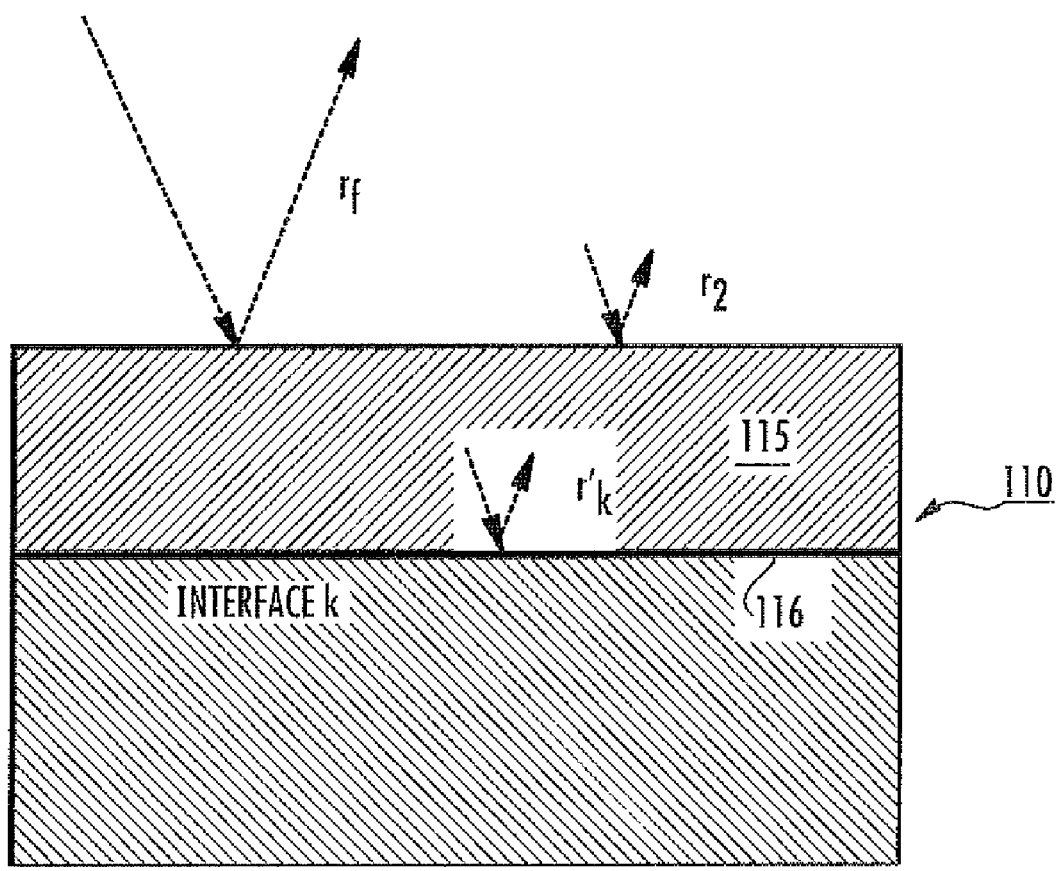
FIG. 3 is a schematic, dross cectional view of a stack of films according to another aspect of the invention similar to FIG. 1 but showing amplitude reflectance of a buried interface.

As discussed above, the magnitude of the reflectance of the interface 116 (mathematically, k) in air can be learned by measuring its intensity reflectance but not the phase of the reflectance in the complex plane. With reference to FIG. 3, when the interface 116(k) is covered by another material 115, the known reflectance is changed. If how the reflectance changes cannot be computed in a simple way, then having learned anything about that reflectance is of no use. Fortunately, there is a straightforward way to relate this to the amplitude reflectance of the interface in air.

In *Optical Properties of Thin Solid Films* (Dover Publications, Inc., Mineola, USA, 1991), O. S. Heavens gives an expression for the amplitude reflectance of a film in terms of the reflectance of the two interfaces of the film:

$$r_{film} = \frac{r_{top} + r_{bot}e^{-i2\delta}}{1 + r_{top}r_{bot}e^{-i2\delta}}. \quad 18$$

where $\delta$ is the optical phase change $$\delta = \frac{2\pi d \sqrt{\varepsilon_2 - \varepsilon_{inc}\sin^2(\theta_{inc})}}{\lambda_0},$$

directly proportional to the physical thickness of the film. If rtop is replaced with r2 (the Fresnel coefficient for reflectance off an infinite slab of the film material with dielectric constant ∈2), and rbot is allowed to be $r_k'$, the reflectance of the multilayer stack when the entrance medium is an infinite slab of film material, then the reflectance of the film's top interface can be written as;

$$r(f_1) = \frac{r_2 + r_k'e^{-i2\delta_2}}{1 + r_2 r_k'e^{-i2\delta_2}}. \quad 19$$

When the thickness of the film goes to zero, the exponential equals 1 and the film reflectance must be identical to $r_k$. This allows $r_k'$ to be solved in terms of $r_k$ as:

$$r_k' = \frac{r_k - r_2}{1 - r_2 r_k}. \quad 20$$

This provides an estimate of $r_k'$ that is partially independent of the preceding film stack, since $r_2$ does not depend on it at all and $r_k$ has been modified, keeping only the phase determined by the film stack calculation.

The Bootstrap Method.

In light of the foregoing introduction, a Bootstrap method for film deposition and refinement is described in the following sections; more particularly, steps to perform Bootstrap refinement of the optical model of a thin film stack are provided as follows.

Step 1. Determine the reflectance of an existing film stack prior to the deposition of a new layer.

The reflectance of a film stack provides some information regarding the complex amplitude reflectance that can be used to refine the model of the reflectance, and that is totally independent of any modeling. If one does not measure reflectance directly, it can be obtained by noting that transmission plus reflectance for an absorption-free thin film stack is unity.

The relationship between the amplitude and intensity reflectance is that the intensity reflectance is the absolute square of the amplitude reflectance. Considering the amplitude reflectance for a moment, it will be clear that it can be expressed in standard Cartesian coordinates on a complex plane, or in complex polar coordinates:

$$r_k = a + ib = |r_k|e^{i\phi_k} \quad 1$$
$$|r_k| = \sqrt{a^2 + b^2}$$
$$\phi_k = \tan^{-1}\left(\frac{b}{a}\right).$$

If the amplitude reflectance is expressed in polar coordinates, it is the magnitude of the amplitude reflectance that is provided by a measure of intensity reflectance, $|r_k|=\sqrt{R_k}$.

It is possible at this point to replace the magnitude of the amplitude reflectivity in Equation 1, $|r_k|$, with the square root of the intensity reflectance. This can be done whenever the anticipated error in future reflectance values due to errors in this initial measurement of $R_k$ is expected to be small. How to obtain this relationship is shown in the following.

Calculating the Worst-Case Future Reflectance

The standard deviation of the magnitude of the amplitude reflectance is given by Equation 3:

$$|r_k| = \sqrt{R_k} \quad 3$$
$$\varepsilon_{|r_k|} = \frac{1}{\sqrt{R_k}}\varepsilon_{R_k}$$
$$\sigma_{|r_k|} = \frac{\sigma_{R_k}}{\sqrt{R_k}}.$$

In the worst-case scenario, Rk is a minimum (the amplitude reflection is on the real axis nearest the origin). This would make the error in magnitude relatively larger. Further, the next layer could result in this vector being advanced by $\pi$, crossing the real axis at the furthest point from the origin, producing a reflectance maximum. Again, in the worst case scenario, the maximum reflectance that could be generated as a result of the observed Rk is:

$$R_{max}(\max) = \left(\frac{(1+r_2^2)R_k^{1/2} - 2r_2}{1 + r_2^2 - 2r_2 R_k^{1/2}}\right)^2. \quad 4$$

To assure that replacing the reflectance amplitude with a measured value does not affect future reflectance measurements by more than the standard deviation of the reflectance measurement, the worst-case scenario must be known. This is:

$$\sigma_{R_{max}}(\max) = \frac{(r_2^2 - 1)^2(1 + r_2^2 - 2r_2 R_k^{-1/2})}{(1 + r_2^2 - 2r_2 R_k^{1/2})^3}\sigma_{R_k}. \quad 5$$

Solving Equation 5 for a factor of 1σ is not easy, and the result is very complicated. However, a numerical solution is straightforward. For silica (r2=−0.2), this value is about Rk=0.19 or 19% reflectance. For niobia (r2=−0.4), the value is about 9% reflectance. In other words, when about to deposit a silica layer, values of $|r_k|$ should not be adjusted when the measured reflectance is less than 19%. When about to deposit a niobia layer, values should not be replaced when the measured reflectance is less than 9%. Instead, assume the modeled reflectance is more accurate in these cases, although it is not necessary to do this often. In the following sections, reasons are discussed to perform bootstrapping only on high-index layers, so by extension, this step is recommended only when a low-index layer is completed.

Step 2: Replace the magnitude of the amplitude reflectance at each wavelength with $\sqrt{R_k}$ whenever measuring a freshly completed silica film with an intensity reflectance greater than 9% or a low-index film with an intensity reflectance greater than the limiting value of the high-index material.

While the intensity measurement provides useful information (most of the time) about the magnitude of reflectance, it unfortunately provides no information about the phase angle in the complex plane, φ. Much of the remainder of the present description relates to how to obtain these phase angles in at least some circumstances.

Monitor Curves Can Give Non-Redundant Calculations of Phase

In most cases, the magnitude of $r_k$ at the base of a niobia layer can be obtained from the measured reflectance of the filth stack terminating in a fresh silica layer. The phase of the amplitude reflectance is more difficult to ascertain, but there are two general approaches. The first is to consider what values of phase are consistent with the final value of reflectance after the next layer is added. To use this information, the optical thickness of the next layer must be known. This is sometimes a redundant calculation since the estimation of optical thickness is usually based on an understanding of the initial reflectance. This is, in fact, a weakness of the usual matrix modeling approach—the calculation is somewhat redundant, Without additional information, redundant calculation would normally be the only option. However, monitor curves are usually recorded during deposition, and those curves contain all the information necessary to compute the phase, $\phi_k$, without the need for redundant calculations. This involves the use of reflectance maxima in the monitor curves.

Step 3. Consider the modeled monitor curve for each wavelength of a niobia (high-index) layer. Discard any monitor curves without maxima in their reflectance during the niobia layer deposition. If none meet this criterion, deposit the layer using a pure model approach.

Based on Equation 14 above, the maxima and minima of a monitor curve can be shown to depend solely on $|r_k'|$, the magnitude of the buried interface's reflectance, and not at all on its phase. The maximum and minimum reflectance during the monitor curve are given by Equation 21:

$$R_{max} = \left(\frac{|r_k'| + |r_2|}{1 + |r_2||r_k'|}\right)^2 \qquad 21$$

$$R_{min} = \left(\frac{|r_k'| - |r_2|}{1 - |r_2||r_k'|}\right)^2$$

Therefore, $R_{max}$ or $R_{min}$ can be used in the monitor curve to convey the magnitude of the buried reflectance. This magnitude can be related to the reflectance as follows.

$$|r_k'| = \frac{\sqrt{R_{max}} - |r_2|}{1 - |r_2|\sqrt{R_{max}}} \text{ or } |r_k'| = \frac{\sqrt{R_{min}} + |r_2|}{1 + |r_2|\sqrt{R_{min}}}; \frac{|r_2| - \sqrt{R_{min}}}{1 - |r_2|\sqrt{R_{min}}}. \qquad 22$$

Thus, from a monitor curve covering at least a quarter wave at the monitor curve wavelength, $|r_k'|$ can be determined.

A caveat to using these equations is as follows. The $R_{min}$ expression has two failings. First, there are two possible solutions for $|r_k'|$ based on $R_{min}$ depending on whether $|r_k'|$ is less than or greater than $|r_2|$. If it is less than $|r_2|$, the right-hand solution is appropriate. If it is greater than $|r_2|$, the left-hand solution is appropriate. The $R_{max}$ expression also has two solutions in principle but can be discarded because it provides nonphysical results. The second problem with the equation from $R_{min}$ is the issue of experimental error. The error expected in the estimation of $|r_k'|$ is related to the error in measurement of $R_{min}$ and $R_{max}$ by Equation 23:

$$\varepsilon_{|r_k'|} = \frac{(1-|r_2^2|)}{2\sqrt{R_{min}}\left(1+|r_2|\sqrt{R_{min}}\right)^2}\varepsilon_{R_{min}} \approx \frac{\varepsilon_{R_{min}}}{2\sqrt{R_{min}}} \qquad 23$$

$$\varepsilon_{|r_k'|} = \frac{(1-|r_2^2|)}{2\sqrt{R_{max}}\left(1-|r_2|\sqrt{R_{max}}\right)^2}\varepsilon_{R_{max}} \approx \frac{\varepsilon_{R_{max}}}{2\sqrt{R_{max}}}.$$

In other words, the error goes up as the key reflectance diminishes. Since the minimum is, by definition, smaller than the maximum, the error expected in estimating $|r_k'|$ goes up accordingly. Thus, for both reasons, the calculation of magnitude from a maximum reflectance (i.e., a minimum in the transmission monitor curve) is preferred.

Choosing the Best Monitor Wavelength

The phase angle φk at the monitor wavelength can be determined from $|r_k'|$ and the Rk as:

$$\cos(\pm\phi_k) = \frac{|r_k'|^2(1+R_k|r_2|^2)-|r_2|^2-R_k}{2|r_2|\sqrt{R_k}\,(1-|r_k'|^2)}. \qquad 25$$

This, of course, provides 2 solutions. Once the phase angle φk from Equation 25 is determined, $r_k'$ can be computed using Equation 20 and a monitor curve can be generated if desired for comparison with the actual to help determine which solution is better. Afterwards, a value for phase at the monitor wavelength should have been obtained that is as correct as possible. It depends, of course, on accurately measuring the maximum reflectance value and Rk. Thus, not all wavelengths are created equal as potential monitor wavelengths. A full-spectrum monitor (acquiring many monitor wavelengths) is the best solution, but if only a single wavelength is available, then there is a systematic approach to choosing the best.

Equation 25 depends, ultimately, on only two measurements: the measurement of the initial reflectance and the measurement of the maximum reflectance. For those wavelengths that exhibit a maximum reflectance during deposition, these can be evaluated quantitatively as possible monitor wavelengths.

It can be shown that the anticipated standard deviation of the phase calculation can be written as:

$$\sigma_{\phi_k} = \sqrt{A\sigma_{R_k}^2 + B\sigma_{R_{max}}^2} \qquad 27$$

$$A = \frac{\left((1+r_2^2)R_k + 2r_2(1+R_k)\sqrt{R_{max}} + (1+r_2^2)R_{max}\right)^2}{4R_k^2\left(4r_2^2R_k(1-R_{max})^2 - \left(\frac{2r_2\sqrt{R_{max}}+(1+r_2^2)R_{max}-}{R_k(1+r_2^2+2r_2\sqrt{R_{max}})}\right)^2\right)}$$

$$B = \frac{(1-R_k)^2\left(r_2+(1+r_2^2)\sqrt{R_{max}}+r_2R_{max}\right)^2}{R_{max}(1-R_{max})^2\left(\frac{4r_2^2R_k(1-R_{max})^2-}{\left(\frac{2r_2\sqrt{R_{max}}+(1+r_2^2)R_{max}-}{R_k(1+r_2^2+2r_2\sqrt{R_{max}})}\right)^2}\right)}.$$

This equation is helpful selecting the best monitor wavelength for the purpose of determining the phase of the amplitude reflectivity at the monitor wavelength.

Figure 4:
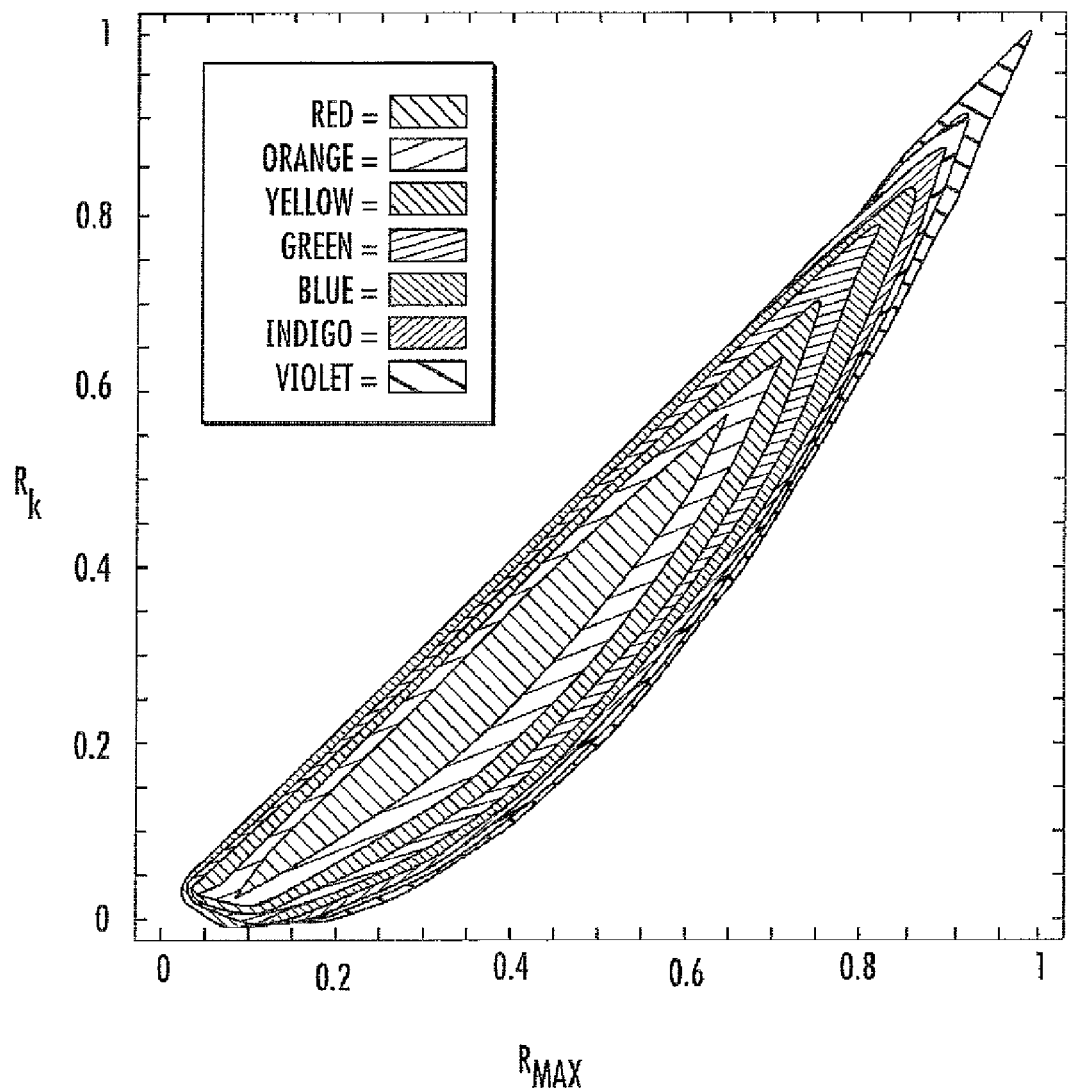
FIG. 4 is a representation of regions of permissible values of Rk and Rmax, particularly showing lowest values of $\sigma_\phi k$ (for silica according to an aspect of the invention.

FIG. 4 shows a representation of the regions of permissible values of Rk and Rmax, with a color code for the lowest values of $\Sigma_{100}$ k for silica (assuming r2=−0.2 and the standard deviation of the reflectance measurements is 0.003). The lowest value possible under these conditions is 0.0262 radians (1.5 degrees). The lower axis, Rmax, represents possible values of Rmax, while the left axis, Rk, gives possible values of Rk. Note that large regions of reflectance are not possible—there are many combinations of Rk and Rmax that cannot coexist. On the boundaries of those disallowed regions, the error in estimating the phase angle, φk, becomes infinite.

Figure 5:
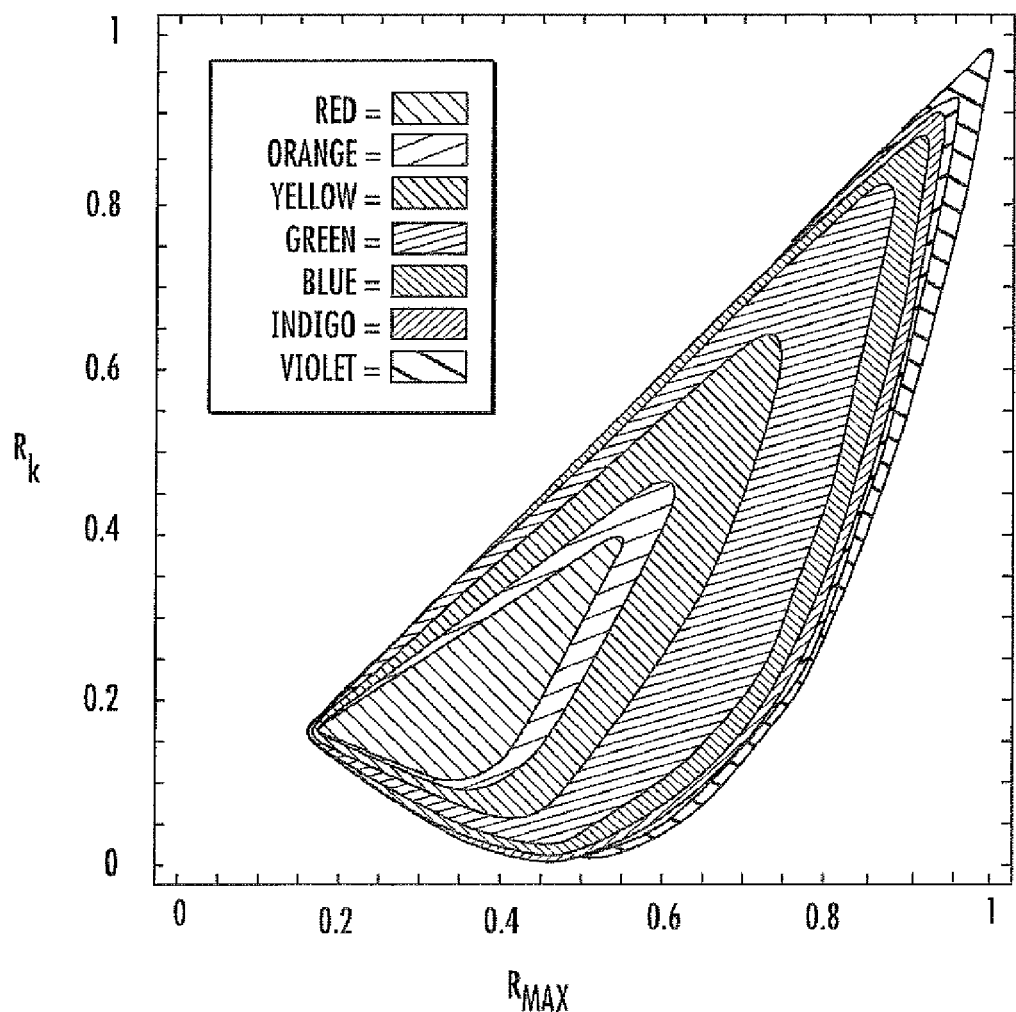
FIG. 5 is similar to FIG. 4 but for niobia according to another aspect of the invention.

The same plot for niobia, assuming $r_2=-0.4$, is given in FIG. 5. The minimum value of error here under the same conditions is 0.00875 radians (0.5 degrees)—a much better phase calculation.

Figure 6:
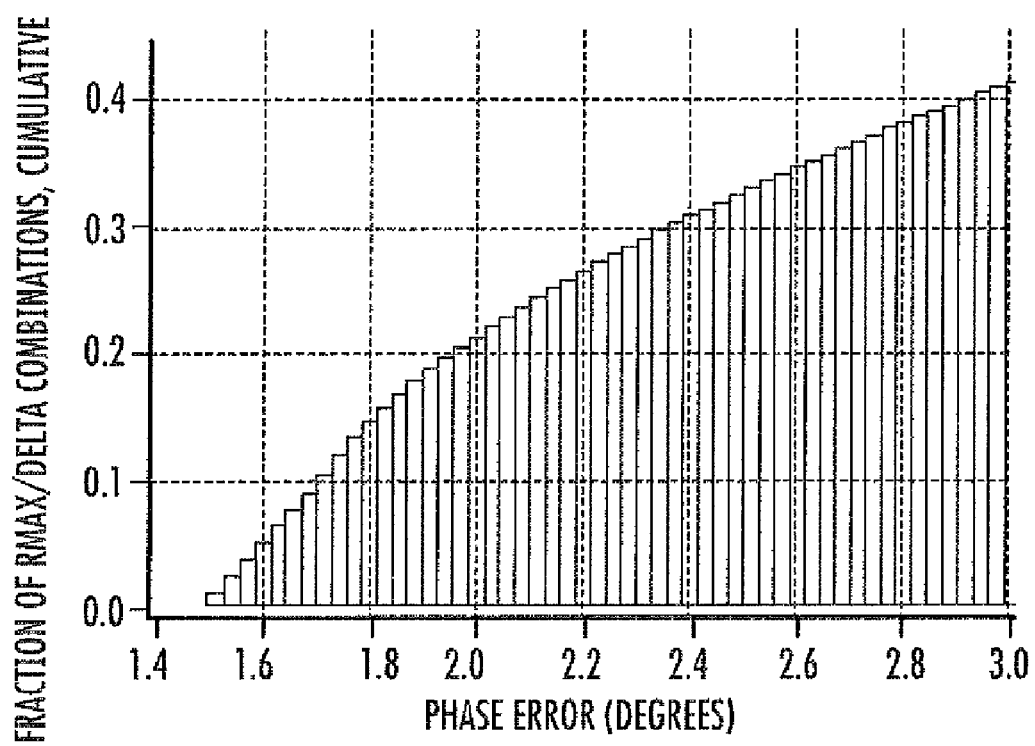
FIG. 6 is a histogram for silica as in FIG. 4.
Figure 7:
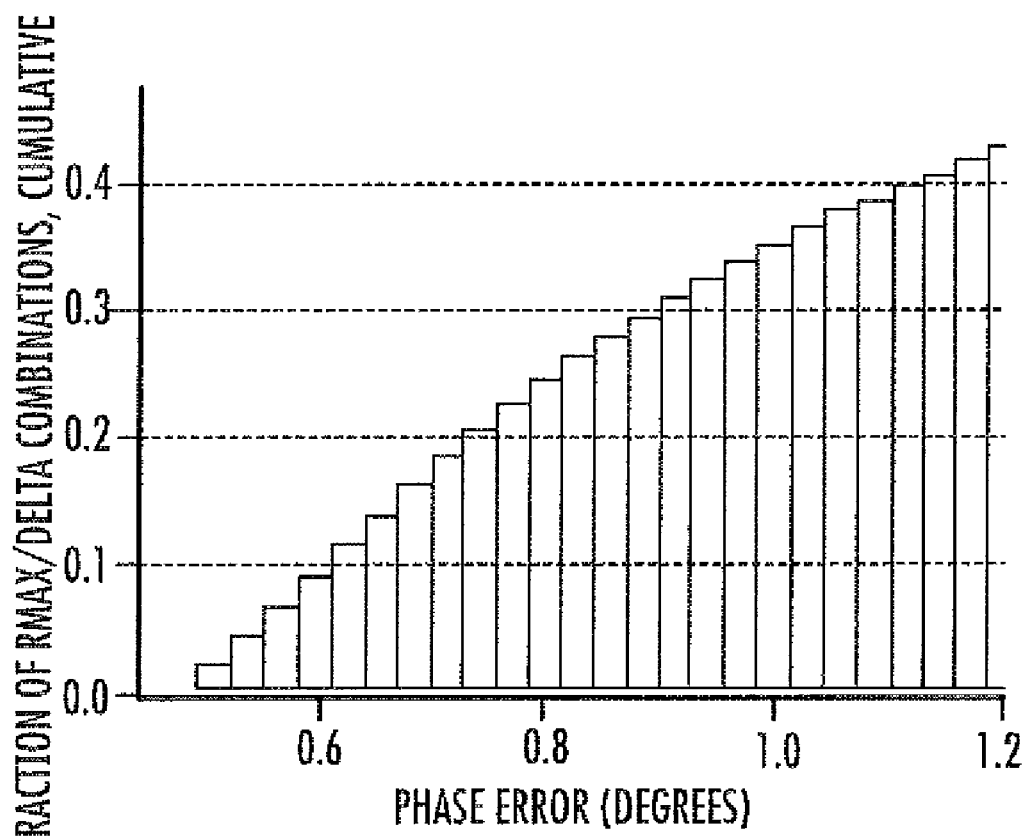
FIG. 7 is a histogram for niobia as in FIG. 5.

It is possible to develop a histogram of the number of combinations of allowed Rmax and Rk that provide a specific level of error in φk. This is accomplished first by considering the range of possible Rmax values when depositing a layer: it cannot, as FIGS. 4 and 5 illustrate, be less than the reflectance of the thin film material being deposited itself (e.g., Rmax for niobia in FIG. 5 cannot be less than $-0.4^2=0.2$ as shown in a leftmost portion of FIG. 5 in dark yellow). Possible values of Rk can be evaluated for each value of Rmax, and the values of phase precision those values provide can be determined using Equation 27. This is accomplished by dividing the phase thickness of the top layer into increments and computing the reflectance at each increment (this is done because the reactances at the turning points are more likely than those in between the turning point values). In the end, a histogram of the resulting precision values can be formed and a determination made as to how likely each will appear for a given film material. This has been done for silica (assuming $r_2=-0.2$, and reflectance standard deviations of 0.003) and for niobia (assuming $r_2=-0.4$) as shown respectively in FIGS. 6 and 7.

For silica, 30% of all observed combinations will have a phase error given by Equation 24 that is less than 2.4 degrees. No values less than about 1.5 degrees error in φk is possible for silica under these conditions. For niobia, the same fraction will have φk errors less than 0.9 degrees, as illustrated in the FIG. 7, also derived from a full numeric simulation.

Thus, the calculated phase error of possible monitor wavelengths will tend to be considerably better for niobia films than for silica. If a limit of 0.9 degrees phase error is placed on the monitors before this calculation is performed, only niobia will give possible monitor wavelengths, and 30% of all wavelengths (overall) will meet this criterion. On some layers, it is possible that no wavelengths will meet this criterion, while on others many may do so.

Step 4. For the remaining possible monitor wavelengths in a niobia layer deposition, determine the anticipated standard deviation in $\phi_k$. Discard any with σ greater than 0.9 degrees (0.016 radians). If none remain, proceed with a pure model deposition.

For low-index layers, bootstrapping is not recommended. For layers with larger magnitudes of $r_2$ (such as niobia), the precision of the bootstrap is almost always better, but there is no guarantee that a specific layer will include a set of $R_k$ and $R_{max}$ values anticipated to provide excellent precision in calculating the phase φk.

If no wavelength with an anticipated reflectance maximum meets this criterion, modeling alone should be relied upon to deposit the layer until a suitable bootstrap layer is reached.

An ingenious characteristic about this calculation is that it provides φk —and thus also $\phi_k$'—that is consistent with the monitor curve and is independent of δ, the phase thickness of the film. Once a valid solution for rk is determined, the valid solution for $r_k$' can be obtained. Thus, the final transmission value at the monitor curve wavelength can be used to determine what value of δ is most accurate for the monitor wavelength.

If a wavelength meets the criterion specified above, then consideration should be given as to whether the anticipated end of the layer will have a reflectance, Rf, suitable for estimating δ, the phase thickness of the layer with some precision. This calculation is performed with Equation 26, where δ depends on Rf and rk'.

$$\delta = \frac{\phi_k'}{2} \pm \frac{1}{2}\cos^{-1}\left(\frac{R_f + R_f|r_2|^2|r_k'|^2 - |r_2|^2 - |r_k'|^2}{2|r_2||r_k'|(1-R_f)}\right). \quad 26$$

This equation provides fairly unique solutions for δ that can be used to correct the reflectance at all wavelengths. The possible solutions for δ that are obtained can be tested against the observed monitor curve to determine which is correct.

For a given monitor curve with a given expectation of Rmax, and with a known value of r2, the sensitivity of δ to errors in Rf can be determined according to Equation 28:

$$\sigma_\delta = \left|\frac{(1-|r_2^2|)(1-R_{max})}{2(R_f-1)\sqrt{A}}\right|\sigma_{R_f} \quad 28$$

$$A = (R_{max} - R_f)\begin{pmatrix} 2|r_2^2|(2R_{max}R_f + R_f - R_{max} - 2) - \\ (1+|r_2^4|)(R_{max} - R_f) + \\ 4(|r_2|+|r_2^3|)(1-R_f)\sqrt{R_{max}} \end{pmatrix}.$$

Figure 8:
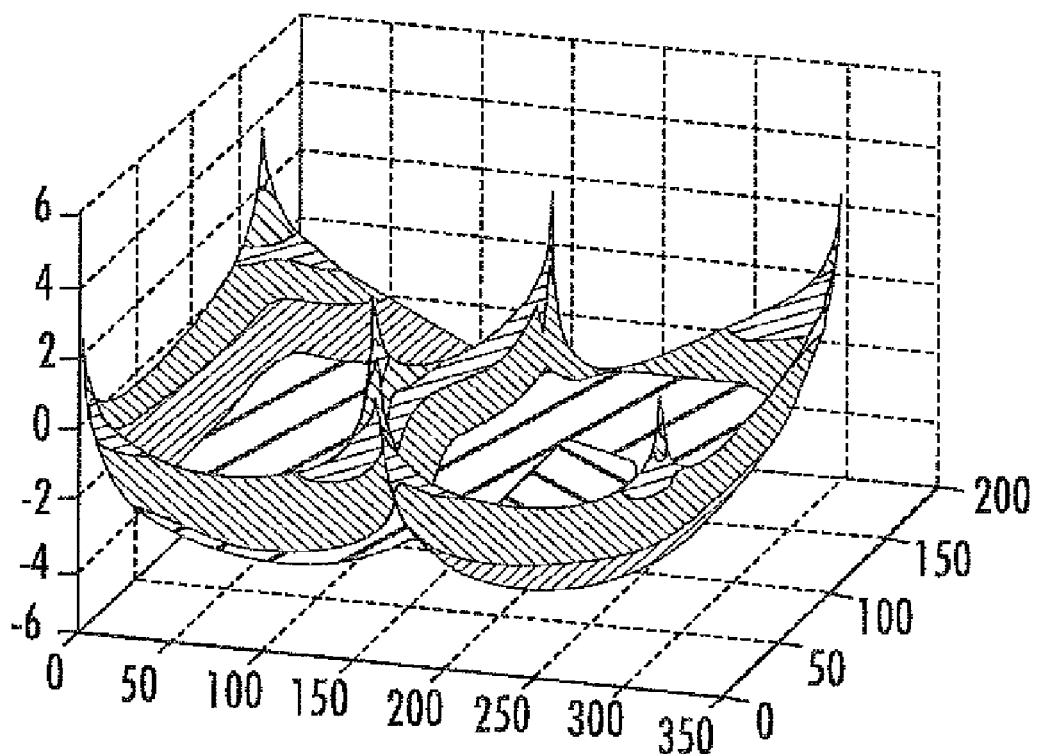
FIG. 8 is a perspective plot showing an error logarithm versus Rmax and δ in accordance with an aspect of the invention.
Figure 8:
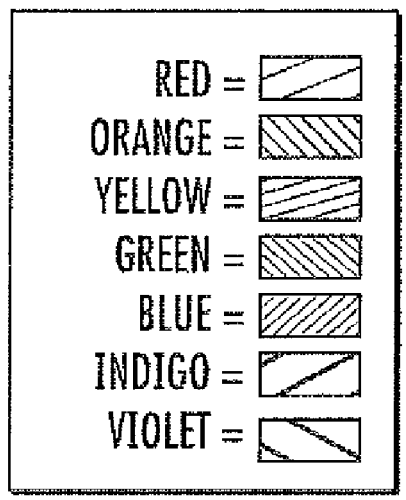

If the type of numerical analysis above using Equation 28 is repeated, a plot as shown in FIG. 8 is obtained (shown as the logarithm of error vs. Rmax and δ because otherwise the scale would be difficult to see). This plot is made over the entire range of possible values of Rmax between $r_2^2$ and 1 (on the receding axis) and δ angle between 0 and 2π (the front axis).

Figure 9:
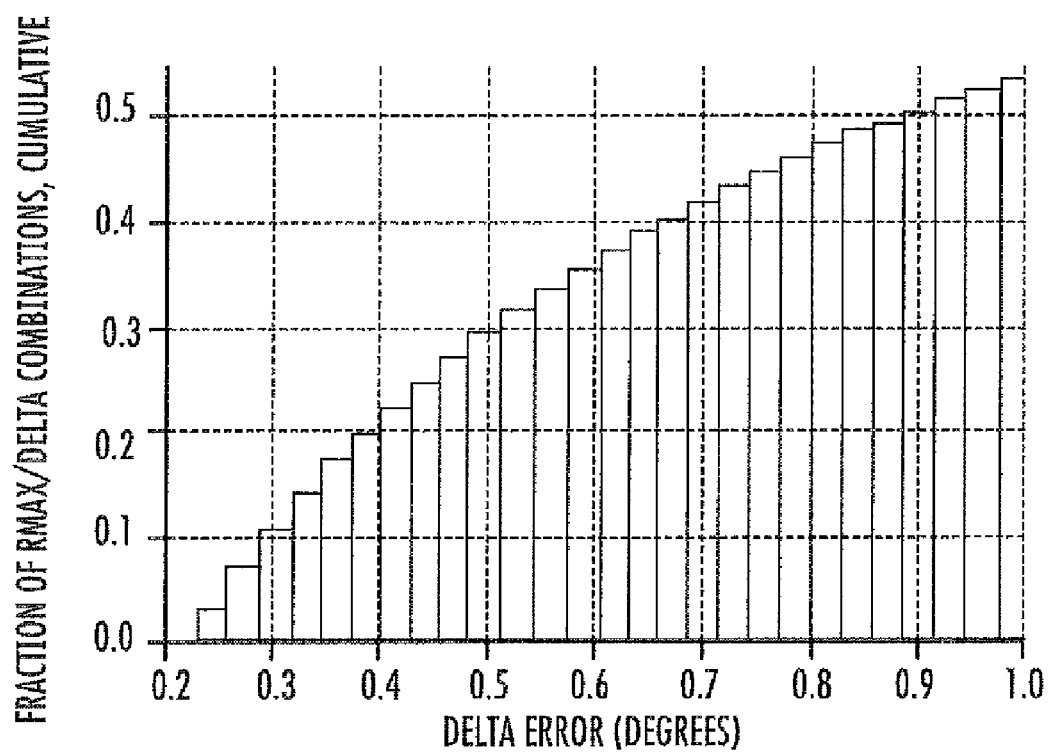
FIG. 9 is a histogram of FIG. 8 data.

The data in FIG. 8 can also be rendered as a histogram as shown in FIG. 9. The histogram in FIG. 9 implies that the error in phase thickness is usually satisfactory compared to the error in φk. At a cutoff of 0.9 degrees error in δ, about 51% of the remaining monitor wavelengths for niobia, for instance, should be usable. Thus, given a good monitor wavelength for determining the phase angle φk, there is a good chance of having one that also provides a good precision in δ.

To conserve time, and when modeling is running fairly well, it is reasonable to only select monitor wavelengths for niobia (in a silica/niobia stack), and only when they meet these two criteria (standard deviation of φk<0.9 degrees, and standard deviation of δ<0.9 degrees at the end of the layer). When no monitor wavelengths meet these criteria, it is reasonable to proceed with a pure model matrix approach to depositing the next layer.

Step 5. Compute the expected error in δ for the remaining wavelengths at the target thickness of the niobia layer. If no wavelengths have an error less than 0.9 degrees, proceed with a full model deposition of the layer. If some do meet this criterion, select the lowest error in this category, Reflectance of a New Film and Determination of the Old Phase at Wavelengths Other Than the Monitor Wavelength.

Why bother with determining the φk and δ from a monitor curve as precisely as possible? First, if a monitor wavelength for bootstrapping has been selected successfully, all connection to the previous dependence on the matrix calculation for the monitor wavelength may be avoided. For all other wavelengths, there is at least the opportunity to determine the magnitude of rk, but only the original modeled estimate of phase. The question arises: how to "repair" the phases of all other wavelengths? Since in a single-channel monitor there are no monitor curves at those wavelengths, the phase at each wavelength cannot be directly obtained. (If there was spectrograph recording all wavelengths all of the time, such as with an FTIR system, the steps provided below would not be needed). However, to reach this point in bootstrapping, there must be a good value for δ for the monitor wavelength, plus good values of Rmax and Rk. With this, at least some of the other measurements can be "fixed" to accord with measurements already taken. This will restrict errors to those of a single layer at the worst for those wavelengths where the following calculation is possible.

From δ for the monitor wavelength, the physical thickness of the layer consistent with the modeled refractive index of the film material can be estimated. This physical thickness and the modeled refractive index of the film can be used to estimate δ for all other wavelengths.

Step 6. Compute the value of δ for all wavelengths based on the value calculated for the monitor wavelength, Returning to Equation 16 and replacing rk' with the definition in Equation 20, the following is obtained:

$$r_f = \frac{r_2(1 - r_2 r_k) + (r_k - r_2)(\cos(2\delta) - i\sin(2\delta))}{1 - r_2 r_k + r_k(r_k - r_2)(\cos(2\delta) - i\sin(2\delta))}. \quad 29$$

In Equation 29, the exponential has been replaced with a trigonometric expression using Euler's relation. If $r_k$ is replaced with a+i b, a conventional expression for $r_f$ can be obtained. The complex conjugate of $r_f$ can be formed and the product taken of the two. This provides the intensity reflectance of the top interface in terms of values from the new film, plus a and b. The following can then replace a and b:

$$a = \cos(\phi_k)\sqrt{R_k}$$

$$b = \sin(\phi_k)\sqrt{R_k} \quad 30.$$

where use is made of the intensity reflectance measured in vacuum for interface k to represent the magnitude of the amplitude reflectance vector at the interface k in vacuum.

The resulting expression can be simplified as Equation 31:

$$R_f = \frac{2r_2^2 + R_k(1 + r_2^4) + 2r_2 Q}{1 + r_2^4 + 2r_2^2 R_k + 2r_2 Q} \quad 31$$

$$Q = r_2^2 R_k^{1/2} \cos(2\delta + \phi_k) + R_k^{1/2} \cos(2\delta - \phi_k) -$$

$$r_2(1 + R_k)\cos(2\delta) - (1 + r_2^2) R_k^{1/2} \cos(\phi_k).$$

In this expression, everything is known EXCEPT the phase angle φ at interface k, allowing it to be determined from the measurement of intensity reflectance at the subsequent interface, Dispensing with numerical solution methods, this expression can be solved for the Cosine of the angle:

$$\cos(\phi_k) = \left(\frac{A(1 + r_2^2)\sin(\delta) \pm B\cos(\delta)}{C}\right) \quad 32$$

$$A = R_f + r_2^4(R_f - R_k) - R_k + 2r_2^2\left(\frac{(1 - R_f)(1 + R_k)\cos(2\delta) -}{(1 - R_f R_k)}\right)$$

$$B = \sqrt{D(1 + r_2^{12}) + F(r_2^2 + r_2^{10}) + G(r_2^4 + r_2^8) + Hr_2^6}$$

-continued $$C = \sin(\delta)(4r_2(1 - R_f)R_k^{1/2}(2r_2^2 \cos(2\delta) - 1 - r_2^4))$$

$$D = -(R_f - R_k)^2$$

$$F = 2\left(\begin{array}{c}R_k(2 + R_k) + R_f^2(1 + 2R_k) + 2R_f(1 - 5R_k + R_k^2) - \\ 2(1 - R_f)(1 - R_k)(R_f + R_k)\cos(2\delta)\end{array}\right)$$

$$G = -6 - 4R_f - 5R_f^2 - 4R_k + 38R_f R_k - 4R_f^2 R_k - 5R_k^2 - 4R_f R_k^2 -$$

$$6R_f^2 R_k^2 + 8(1 - R_f^2)(1 - R_k^2)\cos(2\delta) - 2(1 - R_f)^2(1 - R_k)^2 \cos(4\delta)$$

$$H = 4\left(\begin{array}{c}3 + 2R_f^2 - 10R_f R_k + 2R_k^2 + 3R_f^2 R_k^2 - \\ 2(1 - R_f)(1 - R_k)(2 + R_f + R_k + 2R_f R_k)\cos(2\delta) + \\ (1 - R_f)^2(1 - R_k)^2 \cos(4\delta)\end{array}\right).$$

In principle, Equation 32 can be used to solve for the phase angle. By doing so, the deposition system process control is effectively "bootstrapped" by detaching the system completely from everything that came before the last layer. Equation 32 provides four (4) solutions for the phase angle; two come from the +/− portion of the calculation; two more from the fact that cosine is an even function, so positive and negative angles both work equally well. However, only two of these solutions are consistent with the measured value of $R_f$. Thus, solutions should be checked via Equation 31 for validity. Only two solutions should be left after this process is complete.

Step 7. Compute the two possible values of phase angle for each wavelength other than the monitor wavelength.

Estimating Error for Non-Monitor Wavelengths

The phase angle is dependent on three reflectivity measurements ($R_{max}$, $R_f$ and $R_k$), those being scrambled together in Equation 32. While this works well for a hypothetical system with no noise, a real spectrometer exhibits errors in measurement of the intensity transmittance.

Based on work already done, the analysis of Equation 32 is fairly straightforward for extending phase information to other wavelengths. The following expression can be constructed from it:

$$\varepsilon_{\phi_k} = \frac{-1}{\sin(\phi_k)}\left(\left(\frac{\partial \cos(\phi_k)}{\partial R_k}\right)\varepsilon_{R_k} + \left(\frac{\partial \cos(\phi_k)}{\partial R_f}\right)\varepsilon_{R_f} + \left(\frac{\partial \cos(\phi_k)}{\partial \delta}\right)\varepsilon_\delta\right) \quad 33$$

$$\sigma_{\phi_k} \approx \frac{\sigma_R}{|\sin(\phi_k)|}\left(\left(\frac{\partial \cos(\phi_k)}{\partial R_k}\right)^2 + \left(\frac{\partial \cos(\phi_k)}{\partial R_f}\right)^2\right)^{1/2}.$$

In Equation 33 error in phase thickness has been omitted from the calculation since it is of minor concern at this stage. The phase thickness was settled previously for the sake of argument; therefore, making that approximation, computing the sine of the angle and the sensitivity of the cosine functions to errors in $R_k$ and $R_f$ remain. There is a subtle issue to be considered at this point. What angle should be focused on—the modeled angle or the computed angle using Equations 31/32? In principle, both values are available.

Thus, the conservative answer to the foregoing question is "both", Assume, for example, that the model has a complex reflectance rk at a given wavelength from which the phase angle φk and the predicted value of Rk can be obtained. Using a best estimate of the phase thickness at the wavelength, Rf can be computed using Equation 31, Next, compute the phase angle using Equation 32 after varying Rk and Rf each by a small amount—e.g., by $10^{-5}$, $1/100^{th}$ of a percent transmission. Since the modeled phase is known exactly, it will be trivial to identify which results are the ones closest to the modeled phase; therefore, the sensitivities are computed as:

$$\frac{\partial \cos(\phi_k)}{\partial R_k} \approx \frac{\cos(\phi_k(R_{k,m}, R_{f,m}, \delta)) - \cos(\phi_k(R_{k,m} - 10^{-5}, R_{f,m}, \delta))}{10^{-5}} \quad 34$$

$$\frac{\partial \cos(\phi_k)}{\partial R_f} \approx \frac{\cos(\phi_k(R_{k,m}, R_{f,m}, \delta)) - \cos(\phi_k(R_{k,m}, R_{f,m} - 10^{-5}, \delta))}{10^{-5}}.$$

From the model, the sine of the phase angle that appears in Equation 33 is trivial to obtain.

Thus, the standard deviation of the phase calculation can be estimated from the model. If the model were absolutely trustworthy, this would be sufficient; however, this is not the case.

Step 8. Using information extracted from the model for $r_k$ at each wavelength and the computed best value of $\delta$, compute the estimated standard deviation of phase at all wavelengths except the monitor.

Since the model is not completely trustworthy, the process is repeated using values taken from the calculated value of phase closest to the model value of phase. In other words, for the two possible values of $\phi k$, the one closest numerically to the model phase is selected. Now, keying on that value, compute the sensitivities according to Equation 34 using the measured values of $R_k$, $R_f$ and the estimate of $\delta$ for the wavelength being tested.

Step 9. Using the computed phase closest to the model phase for $r_k$ at each wavelength, the measured $R_f$ and $R_k$ values and the computed best value of $\delta$, compute the estimated standard deviation of phase at all wavelengths for which the magnitude of $r_k$ was estimated (Step 2) other than the monitor.

Now, compute the estimated error in phase as follows:

$$\sigma_{100_k}(\text{estimated}) = (\sigma_{\phi_k}^2(\text{model}) + \sigma_{\phi_k}^2(\text{calculated}))^{1/2} \quad 35.$$

What are the probable limits to this calculation? A bit of experimentation suggests that the value of standard deviation in phase angle could be between about that of the monitor measurement (on the low end) to nearly infinite. A sufficient approach is to replace the modeled values with calculated values only if a rather conservative cutoff is obtained. If the error estimates are less than about 1.3 degrees from Equation 35 (square root of two times 0.9), and if the reflectance was greater than 9 percent at the start of the layer (Step 2), then the model and calculated values are averaged together to obtain a new estimate. If either the phase error OR the reflectance criteria are not met, the estimate is returned alone to the model.

Step 10. If the phase error estimate is less than 1.3 degrees AND the criterion of Step 2 is met, average the calculated and modeled reflectance and phase values to obtain a new value that will be used in all future modeling at that wavelength.

A further refinement of this approach is to fit the phase values obtained above to a Kramers-Kronig model of the phase to fill in values of the phase that have not been determined previously.

While preferred embodiments of the invention have been shown and described, those of ordinary skill in the art will recognize that changes and modifications may be made to the foregoing examples without departing from the scope and spirit of the invention. Furthermore, those of ordinary skill in the art will appreciate that the foregoing description is by way of example only, and is not intended to limit the invention so further described in such appended claims. It is intended to claim all such changes and modifications as fall within the scope of the appended claims and their equivalents.

That which is claimed is:

1. A method for forming a thin film interference filter comprising:
    measuring a reflectance of a stack of a plurality of films;
    modeling a monitor curve at a modeled monitor wavelength for a topmost layer to be deposited on the stack of the plurality of films;
    depositing the topmost layer on the stack of the plurality of films; and
    recording a plurality of monitor curves during the deposition, each monitor curve being recorded for a different monitor wavelength of the topmost layer; wherein
    the topmost layer is a high index of refraction layer that exhibits a wavelength that is determined according to the characteristics of either the modeled monitor curve or one of the recorded monitor curves; and
    determining an anticipated standard deviation in $\phi\kappa$ for each different monitor wavelength in the high-index of refraction layer and discarding any monitor wavelengths with $\sigma$ greater than 0.9 degrees.

2. The method as in claim 1, further comprising the step of computing expected error in $\delta$ for the monitor wavelengths with $\sigma$ less than 0.9 degrees at a target thickness of the high index of refraction layer.

3. The method according to claim 1, the method further comprising
    determining phase angle $\phi\kappa$ at the modeled monitor wavelength from $|r_k'|$ and $R_k$ using a first equation expressed as:

$$\cos(\pm\phi_k) = \frac{|r_k'|^2(1 + R_k|r_2|^2) - |r_2|^2 - R_k}{2|r_2|\sqrt{R_k}(1 - |r_k'|^2)}; \quad \text{and}$$

estimating $r_k'$ using a second equation and $$r_k' = \frac{r_k - r_2}{1 - r_2 r_k}.$$

4. The method according to claim 1, wherein the step of measuring the reflectance of the stack of the plurality of films comprises measuring the intensity reflectance of the stack, the method further comprising
    determining from the measurement of intensity reflectance at the topmost interface a phase angle $\phi$ at an interface k according to an equation expressed as:

$$\cos(\phi_k) = \left(\frac{A(1 + r_2^2)\sin(\delta) \pm B\cos(\delta)}{C}\right)$$

$$A = R_f + r_2^4(R_f - R_k) - R_k + 2r_2^2((1 - R_f)(1 + R_k)\cos(2\delta) - (1 - R_f R_k))$$

$$B = \sqrt{D(1 + r_2^{12}) + F(r_2^2 + r_2^{10}) + G(r_2^4 + r_2^8) + Hr_2^6}$$

$$C = \sin(\delta)(4r_2(1 - R_f)R_k^{1/2}(2r_2^2\cos(2\delta) - 1 - r_2^4))$$

$$D = -(R_f - R_k)^2$$

$$F = 2\begin{pmatrix} R_k(2 + R_k) + R_f^2(1 + 2R_k) + 2R_f(1 - 5R_k + R_k^2) - \\ 2(1 - R_f)(1 - R_k)(R_f + R_k)\cos(2\delta) \end{pmatrix}$$

$$G = -6 - 4R_f - 5R_f^2 - 4R_k + 38R_f R_k - 4R_f^2 R_k - 5R_k^2 - 4R_f R_k^2 -$$

-continued
$$6R_f^2 R_k^2 + 8(1-R_f^2)(1-R_k^2)\cos(2\delta) - 2(1-R_f)^2(1-R_k)^2\cos(4\delta)$$

$$H = 4\begin{pmatrix} 3 + 2R_f^2 - 10R_f R_k + 2R_k^2 + 3R_f^2 R_k^2 - \\ 2(1-R_f)(1-R_k)(2+R_f+R_k+2R_f R_k)\cos(2\delta) + \\ (1-R_f)^2(1-R_k)^2\cos(4\delta) \end{pmatrix}.$$

5. The method as in claim 4, further comprising the step of validating two resultant solutions according to the expression:

$$R_f = \frac{2r_2^2 + R_k(1+r_2^4) + 2r_2 Q}{1 + r_2^4 + 2r_2^2 R_k + 2r_2 Q}$$

$$Q = r_2^2 R_k^{1/2}\cos(2\delta + \phi_k) + R_k^{1/2}\cos(2\delta - \phi_k) - r_2(1+R_k)\cos(2\delta) - (1+r_2^2)R_k^{1/2}\cos(\phi_k).$$

6. The method as in claim 4, further comprising the step of averaging calculated and modeled reflectance and phase values to obtain a new value to be used in all future modeling at a given wavelength.

7. The method of claim 1, wherein measuring a reflectance includes measuring the transmittance of a stack of a plurality of films and determining the reflectance from the transmittance.

8. The method of claim 1, wherein the high index of refraction material layer is a niobia layer.

9. A method for forming a thin film interference filter comprising:
measuring a reflectance of a stack of a plurality of films;
modeling a monitor curve at a modeled monitor wavelength for a topmost layer to be deposited on the stack of the plurality of films;
depositing the topmost layer on the stack of the plurality of films;
recording a plurality of monitor curves during the deposition, each monitor curve being recorded for a different monitor wavelength of the topmost layer, wherein the topmost layer exhibits a wavelength that is determined according to the characteristics of either the modeled monitor curve or one of the recorded monitor curves; and
computing two possible values of phase angle for each monitor wavelength other than the modeled monitor wavelength.

10. The method of claim 9, wherein measuring a reflectance includes measuring the transmittance of a stack of a plurality of films and determining the reflectance from the transmittance.

11. A method for forming a thin film interference filter comprising:
measuring a reflectance of a stack of a plurality of films;
modeling a monitor curve at a modeled monitor wavelength for a topmost layer to be deposited on the stack of the plurality of films;
depositing the topmost layer on the stack of the plurality of films;
recording a plurality of monitor curves during the deposition, each monitor curve being recorded for a different monitor wavelength of the topmost layer, wherein the topmost layer exhibits a wavelength that is determined according to the characteristics of either the modeled monitor curve or one of the recorded monitor curves; and
using information extracted from the model for $r_k$ at each monitor wavelength and the computed best value of $\delta$, and computing an estimated standard deviation of phase at all monitor wavelengths except the modeled monitor wavelength.

12. The method as in claim 11, further comprising the steps of using the computed phase closest to the model phase for $r_k$ at each monitor wavelength, measured $R_f$ and $R_k$ values and the computed best value of $\delta$, and computing the estimated standard deviation of phase at all monitor wavelengths for which the magnitude of $r_k$ was estimated other than the modeled monitor.

13. The method as in claim 11, further comprising the steps of determining if a phase error estimate is less than about 1.3 degrees and averaging calculated and modeled reflectance and phase values to obtain a new value for use in subsequent modeling at that wavelength.

14. The method of claim 11, wherein measuring a reflectance includes measuring the transmittance of a stack of a plurality of films and determining the reflectance from the transmittance.

15. A method for forming a thin film interference filter comprising:
measuring a reflectance of a stack of a plurality of films;
modeling a monitor curve at a modeled monitor wavelength for a topmost layer to be deposited on the stack of the plurality of films;
depositing the topmost layer on the stack of the plurality of films; and
recording a plurality of monitor curves during the deposition, each monitor curve being recorded for a different monitor wavelength of the topmost layer, wherein the topmost layer exhibits a wavelength that is determined according to the characteristics of either the modeled monitor curve or one of the recorded monitor curves, the top layer having an intensity of reflectance of greater than 9%; and
replacing the magnitude of the amplitude reflectance at each monitor wavelength with $\sqrt{R_k}$.

16. The method of claim 15, wherein measuring a reflectance includes measuring the transmittance of a stack of a plurality of films and determining the reflectance from the transmittance.

17. The method as in claim 15, further comprising the step of averaging calculated and modeled reflectance and phase values to obtain a new value for use in subsequent modeling at that wavelength.

18. The method of claim 15, wherein the topmost layer is a silica layer.

19. A method for forming a thin film interference filter comprising:
measuring a reflectance of a stack of a plurality of films;
modeling a monitor curve at a modeled monitor wavelength for a topmost layer to be deposited on the stack of the plurality of films;
depositing the topmost layer on the stack of the plurality of films; and
recording a plurality of monitor curves during the deposition, each monitor curve being recorded for a different monitor wavelength of the topmost layer;
wherein the topmost layer exhibits a reflectance maximum for at least one of the monitor curves being recorded; and
obtaining a phase for the reflectance using the measured reflectance and the reflectance maximum,
wherein a standard deviation for the phase is found for each of the monitor curves having a reflectance maximum and a reflectance, and a monitor curve is selected such that the standard deviation for the phase is less than a pre-selected value.

20. The method of claim 19 wherein depositing the topmost layer on the stack proceeds according to a pure model deposition if no monitor curve is found having a standard deviation for the phase less than the pre-selected value.

21. The method of claim 20 wherein the topmost layer is a niobia layer and the pre-selected value is 0.9 degrees.

22. The method of claim 20 wherein the topmost layer is a silica layer and the pre-selected value is 2.4 degrees.

23. The method of claim 19 wherein a standard deviation for the reflectance is found for each of the monitor curves having a reflectance maximum; and the monitor curve having the lowest standard deviation for the reflectance is selected to proceed with the thin film layer deposition.

24. The method of claim 23 wherein the thin film deposition proceeds according to a pure model deposition if the standard deviation for the reflectance is larger than or equal to the reflectance of an infinite slab of the material being deposited.

25. The method of claim 24 wherein the material being deposited is silica.

26. The method of claim 24 wherein the material being deposited is niobia.

27. The method of claim 19, wherein measuring a reflectance includes measuring the transmittance of a stack of a plurality of films and determining the reflectance from the transmittance.

* * * * *